United States Patent
Wurtzel et al.

(10) Patent No.: US 9,677,056 B2
(45) Date of Patent: Jun. 13, 2017

(54) METHOD FOR MODIFYING CAROTENOID BIOSYNTHESIS IN PLANTS

(71) Applicant: Research Foundation of The City University of New York, New York, NY (US)

(72) Inventors: Eleanore T. Wurtzel, Riverdale, NY (US); Maria Shumskaya, Bronx, NY (US)

(73) Assignee: Research Foundation of The City University of New York, New York, NY (US)

( * ) Notice: Subject to any disclaimer, the term of this patent is extended or adjusted under 35 U.S.C. 154(b) by 30 days.

(21) Appl. No.: 14/421,661

(22) PCT Filed: Aug. 15, 2013

(86) PCT No.: PCT/US2013/055069
§ 371 (c)(1),
(2) Date: Feb. 13, 2015

(87) PCT Pub. No.: WO2014/028696
PCT Pub. Date: Feb. 20, 2014

(65) Prior Publication Data
US 2015/0315551 A1    Nov. 5, 2015

Related U.S. Application Data

(60) Provisional application No. 61/683,494, filed on Aug. 15, 2012.

(51) Int. Cl.
*C12N 9/10* (2006.01)
*C12N 15/82* (2006.01)
(52) U.S. Cl.
CPC ......... *C12N 9/1085* (2013.01); *C12N 15/825* (2013.01); *C12Y 205/01032* (2013.01)
(58) Field of Classification Search
CPC .................................................. C12N 9/1085
See application file for complete search history.

(56) References Cited

U.S. PATENT DOCUMENTS 7,838,749 B2 * 11/2010 Beyer ............... C12N 9/00
435/419

OTHER PUBLICATIONS

Fu, Z. et al. Theor. Appl. Genet. (2010) vol. 120, No. 4, pp. 709-720 +suppl. 21 pages.*
GenBank Accession GI: 264665604; Apr. 6, 2010.*
Welsch et al., "Provitamin A Accumulation in Cassava (*Manihot esculenta*) Roots Driven by a Single Nucleotide Polymorphism in a Phytoene Synthase Gene", The Plant Cell, vol. 22; pp. 3348-3356, Oct. 2010, www.plantcell.org, 2010 American Society of Plant Biologists.
Li et al., "The Maize Phytoene Synthase Gene Family: Overlapping Roles for Carotenogenesis in Endosperm, Photomorphogenesis, and Thermal Stress Tolerance", Plant Physiology, Jul. 2008, vol. 147, pp. 1334-1346, www.plantphysiol.org, 2008 American Society of Plant Biologists.
Shumskaya et al., "Plastid Localization of the Key Carotenoid Enzyme Phytoene Synthase is Altered by Isozyme, Allelic Variation, and Activity", The Plant Cell, vol. 24, pp. 3725-3741, Sep. 2012, www.plantcell.org, 2012 American Society of Plant Biologists.
International Search Report, PCT/US13/55069, Dec. 16, 2013.
K. A. Palaisa et al: "Contrasting Effects of Selection on Sequence Diversity and Linkage Disequilibrium at Two Phytoene Synthase Loci", The Plant Cell, vol. 15, No. 8, Aug. 1, 2003 (Aug. 1, 2003), pp. 1795-1806, XP55249034, US.
Zhiyuan Fu et al: "Nucleotide diversity and molecular evolution of the PSY1 gene in *Zea mays* compared to some other grass species", Theoretical and Applied Genetics; International Journal of Plant Breeding Research, Springer, Berlin, DE,vol. 120, No. 4, Nov. 3, 2009 (Nov. 3, 2009), pp. 709-720, XP019776223, ISSN: 1432-2242.
European Search Report for PCT/US2013/055069 dated Feb. 18, 2016.

* cited by examiner

*Primary Examiner* — Russell Kallis
(74) *Attorney, Agent, or Firm* — Hoffmann & Baron, LLP

(57) ABSTRACT

Methods are provided for modifying and screening for carotenoid biosynthesis in a plant. The methods are useful for enhancing plant adaptation to climate change and food security, providing increased carotenoid content to a plant, improving stress resistance to climate changes in a plant, and for selecting plants having improved stress resistance to climate changes.

4 Claims, 12 Drawing Sheets

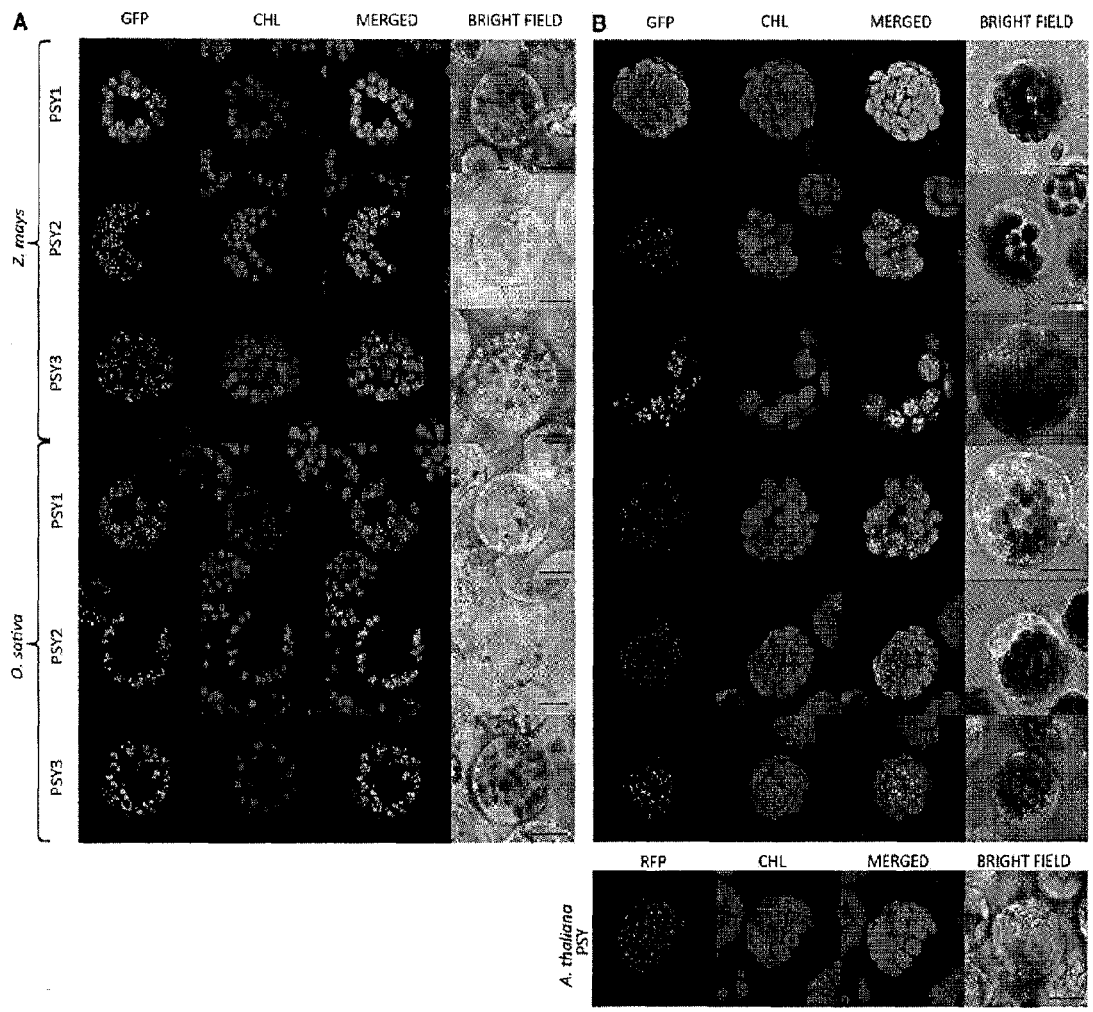

Figure 1. Transient Expression of Various PSY-GFP Fusion Constructs in Leaf Mesophyll Protoplasts.

(A) Expression in etiolated maize protoplasts. All PSYs from maize and rice, except Zm-PSY1, are localized to specific speckles. Zm-PSY1 is localized to stroma and associated to prolamellar bodies. CHL, chlorophyll autofluorescence, concentrated in a partial area of an etioplast.
(B) Expression of Zm-PSYs and Os-PSYs in green maize protoplasts and of At-PSY-RFP in green cowpea protoplasts. All PSY from maize, rice, and *Arabidopsis*, except Zm-PSY1, are localized to specific speckles. Zm-PSY1 is localized to stroma. CHL, chlorophyll autofluorescence, occupying the entire area of a chloroplast.
Bars = 10 μm.

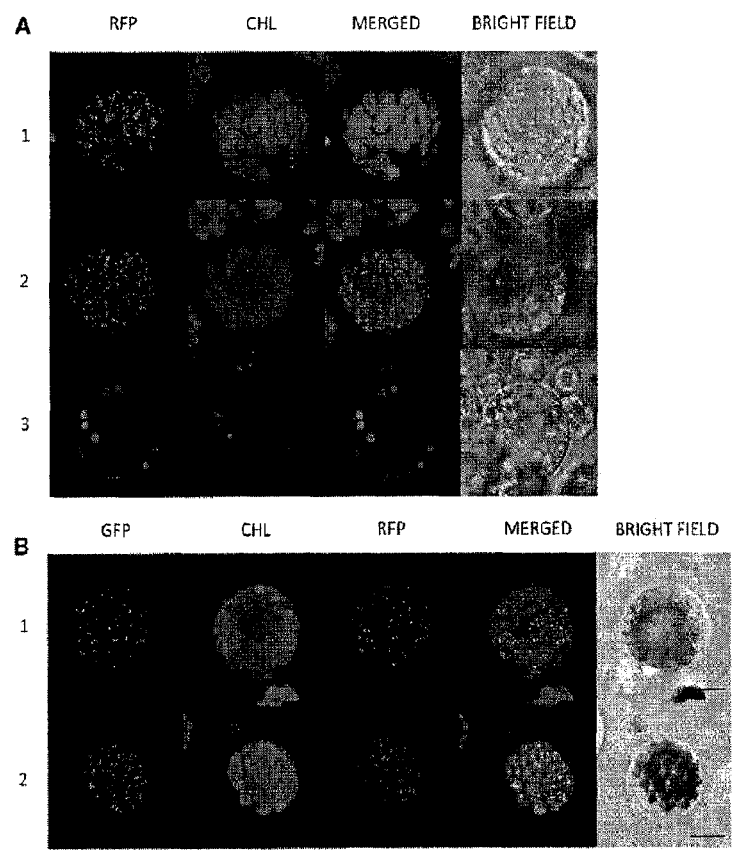

Figure 2. Plastoglobuli Localization of Various Proteins in Mesophyll Protoplasts.

(A) Transient expression of Zm-PG2-RFP, suggesting localization to plastoglobuli. 1, Expression in cowpea cotyledon protoplasts. 2, Expression in green maize protoplasts. 3, Expression in etiolated maize protoplasts. 1 and 2 show plastoglobular localization, and 3 shows stromal localization.
(B) Transient coexpression of Zm-PSY2-GFP (1) and Zm-PSY3-GFP (2) with Zm-PG2-RFP. Zm-PSYs and Zm-PG2 are colocalized, as seen on merged image, indicating plastoglobular localization of Zm-PSY2 and Zm-PSY3.
CHL, chlorophyll autofluorescence. Bars = 10 μm.

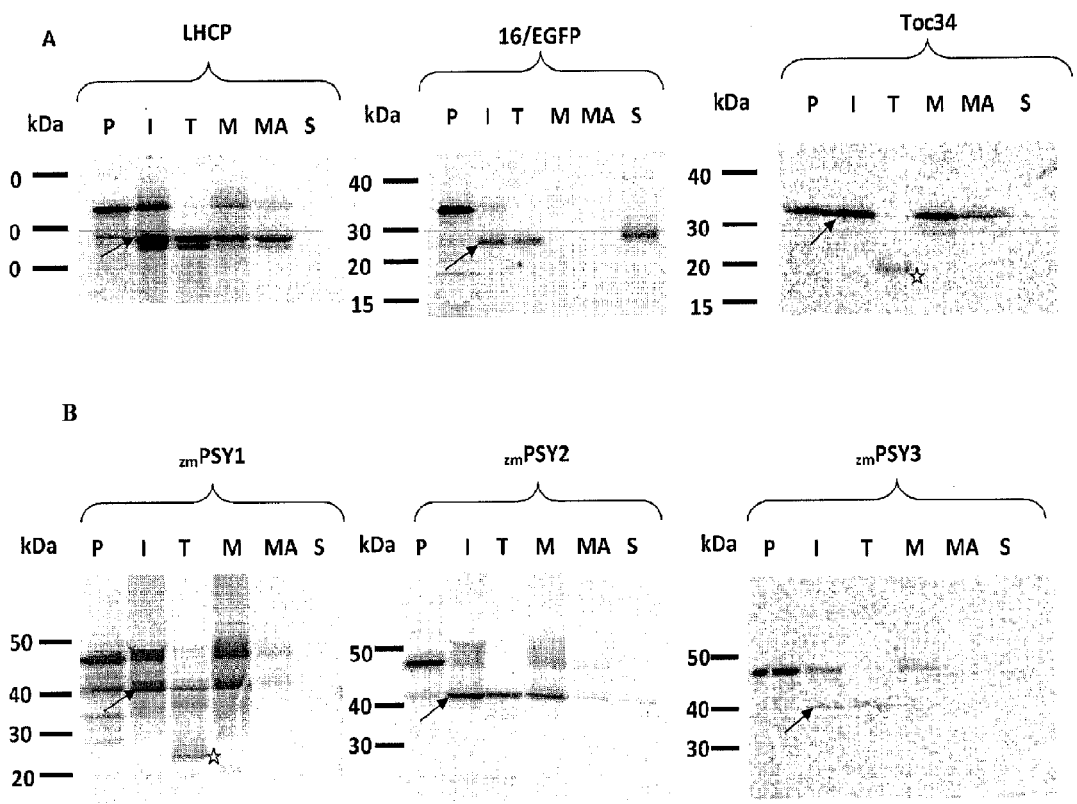

Figure 3. Import of proteins into chloroplasts. Protein precursors were made by *in vitro* transcription/translation and incubated with isolated chloroplasts for import and processing to mature forms. Mature proteins were resistant to post-import thermolysin treatment of chloroplasts and of smaller mass compared to the unimported precursors.
Star – 20 kDa band.
kDa – molecular weight marker
P – precursor (1 µl of the translation mix)
I – import of radiolabelled precursor protein into intact chloroplasts
T – thermolysin treated chloroplasts
M – membrane fraction
MA – purified membrane fraction (after alkaline treatment)
S – soluble fraction

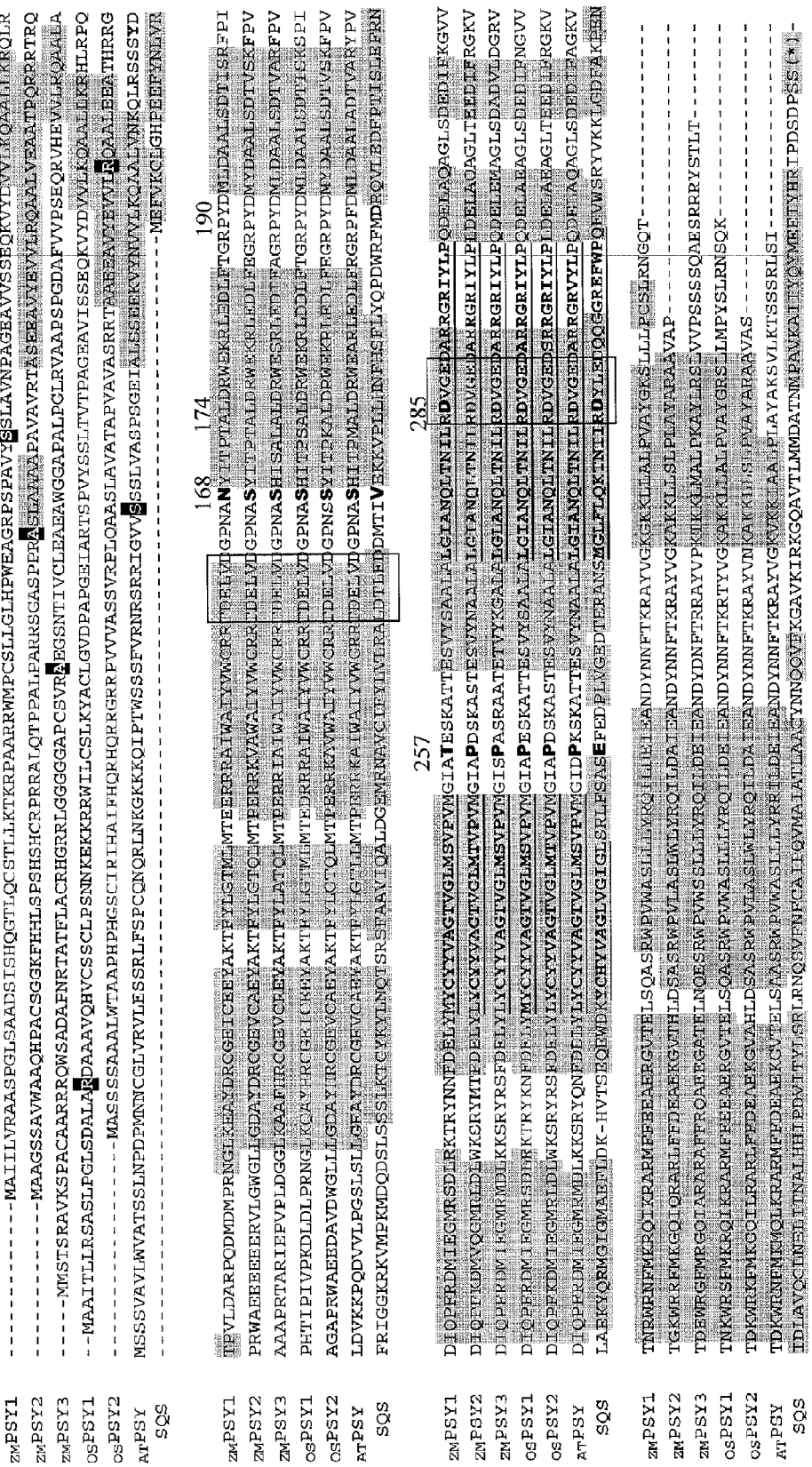
Figure 4. Alignment of PSY amino acid sequences for all enzymes used in experiments adjusted to secondary SQS structure

|  |  |  | 168 | 257 |
|---|---|---|---|---|
| maize PSY1 | ACY70899 | Mo17 yellow | -RRTDELVDGPNANYITPTA- | -MGIAIESKATTESVYSAALALGIANQLTNILRDVGEDARR- |
|  | ACY70890 | BGY white | -RRTDELVDGPNANYITPTA- | -MGIAIESKATTESVYSAALALGIANQLTNILRDVGEDARR- |
|  | ACY70881 | BZN white | -RRTDELVDGPNANYITPTA- | -MGIASESKATTESVYSAALALGIANQLTNILRDVGEDARR- |
|  | ACY70886 | BR1 white | -RRTDELVDGPNANYITPTA- | -MGIAPESKATTESVYSAALALGIANQLTNILRDVGEDARR- |
| eosinte | ACY70878 | Z. m. ssp. Mexicana | -RRTDELVDGPNANYITPTA- | -MGIAIESKATTESVYSAALALGIANQLTNILRDVGEDARR- |
|  | ACY70877 | Z. m. ssp. huehuetangensis | -RRTDELVDGPNANYITPTA- | -MGIAIESKATTESVYSAALALGIANQLTNILRDVGEDARR- |
|  | ACY70874 | Z. diploperennis | -RRTDELVDGPNANYITPTA- | -MGIAPESKATTESVYSAALALGIANQLTNILRDVGEDARR- |
|  | ACY70875 | Z. luxuriantes | -RRTDELVDGPNANYITPTA- | -MGIAPESKATTESVYSAALALGIANQLTNILRDVGEDARR- |
|  | ACY70879 | Z. m. ssp. parviglumis | -RRTDELVDGPNANYITPTA- | -MGIAPESKATTESVYSAALALGIANQLTNILRDVGEDARR- |
| monocots | ACY68563 | 1 Aegilops tauschii | -RRTDELVDGPNASHITPQA- | -MGIAPESKATAESVYGAALALGLANQLTNILRDVGEDARR- |
|  | ACY70867 | Coix lacryma-jobi | -RRTDELVDGPNANYITPTA- | -MGIAPESKATTESVYSAALALGIANQLTNILRDVGEDARR- |
|  | X78814 | N. pseudonarciscuss | -RRTDELVDGHNASHITPSA- | -MGIAPESLAEAESVYNAALALGIANQLTNILRDVGEDARR- |
|  | ABI98829 | Narcissus tazetta | -RRTDELVDGHNASHITPSA- | -MGIAPESLAEAESVYNAALALGIANQLTNILRDVGEDARR- |
|  | AAW28996 | Sorghum bicolor PSY1 | -RRTDELVDGPNANYITPTA- | -MGIAPESKATTESVYSAALALGIANQLTNILRDVGEDATR- |
|  |  | S. bicolor PSY2 | -RRTDELVDGPNASHISAVA- | -MGIAPDSKASTESVYNAALALGIANQLTNILRDVGEDARR- |
|  | AY705390 | S. bicolor PSY3 | -RRTDELVDGPNASHISAVA- | -MGISPDSRAATETVYKGALALGLANQLTNILRDVGEDARR- |
|  | ACY70872 | Tripsacum sp. ZF2009 | -RRTDELVDGPNANYITPTA- | -MGIAPESKATTESVYSAALALGIANQLTNILRDVGEDARR- |
|  | ACF42352 | Triticum aestivum | -RRTDELVDGPNASHITPQA- | -MGIAPDSKATAESVYGAALALGLANQLTNILRDVGEDARR- |
|  | ABW80613 | Thinopyrum ponticum | -RRTDELVDGPNASHITPQA- | -MGIAPESKATAESVYGTALALGLANQLTNILRDVGEDARR- |
| dicots | ACO53104 | Actinidia deliciosa | -RRTDELVDGPNASHITPTA- | -MGIAPDSLATTESVYNAALALGIANQLTNILRDVGEDARR- |
|  | ACT20708 | Brassica rapa | -RRTDELVDGPNASHITPMA- | -MGIDPKSKATTESVYNAALALGIANQLTNILRDVGEDARR- |
|  | ABG72805 | Carica papaya | -RRTEELVDGPNASHITPTA- | -MGIAESQATTESVYNAALALGIANQLTNILRDVGEDARR- |
|  | ABA43898 | Coffea canephora | -RRTDELVDGPNASHITPTA- | -MGIAPESKATVESVYNAALALGIANQLTNILRDVGEDATR- |
|  | ABY86652 | Citrus maxima | -RRTDELVDGPNASYITPAA- | -MGIAPDSQATTESVYNAALALGIANQLTNILRGVGEDAQR- |
|  | AAF33237 | Citrus unshiu | -RRTDELVDGPNASHITPTA- | -MGIAPDSQATTESVYNAALALGIANQLTNILRDVGEDARR- |
|  | ABY86651 | x Citrofortunella mitis | -RRTDELVDGPNASHITPAA- | -MGIAPDSQATTESVYNAALALGIANQLTNILRDVGEDAQR- |
|  | ADC34069 | Cucumis melo | -RRTDELVDGPNASHITPTA- | -MGIAPESQASTESVYNAALALGIANQLTNILRDVGEDARR- |
|  | ABB52068 | D. carota ssp. sativus | -RRTDELVDGPNASHITPQA- | -MGIAPNSQATTESVYNAALALGLANQLTNILRDVGEDARR- |
|  | ACM44688 | Diospyros kaki | -RRTDELVDGHNASHITPTA- | -MGIAPESQATTESVYNAALALGIANQLTNILRDVGEDARR- |
|  | ACU29637 | Elaeagnus umbellate | -RRTDELVDGPNASHITPKA- | -MGIAPESQATTESIYNAALALGISNQLTNILRDVGEDARR- |
|  | BAI47572 | Ipomoea sp. Kenyan | -RRTDELVDGPNASHITPTA- | -MGIAPESKATTESVYNAALALGIANQLTNILRDVGEDARR- |
|  | ACY42664 | Manihot esculenta PSY1 | -RRTDELVDGPNASHITPTA- | -MGIAPESQASTESVYNAALALGIANQLTNILRDVGEDARR- |
|  | ACY42665 | Manihot esculenta PSY2 | -RRTDELVDGPNASHITPTA- | -MGIAPESQASTESVYNAALALGIANQLTNILRDVGEDARR- |
|  | AAR86104 | Mcmordica charantia | -RRTDELVDGPNASHITPTA- | -MGIAPDSEASTESVYNAALALGIANQLTNILRDVGEDARR- |
|  | ADK25054 | Nicotiana tabacum | -RRTDELVDGPNASHITPQA- | -MGIAPESKATTESVYNAALALGLANQLTNILRDVGEDARR- |
|  | AAR87868 | Oncidium Gower Ramsey | -RRTDELVDGPNASHITPSA- | -MGIAPESDATTESVYNAALALGIANQLTNILRDVGEDATR- |
|  | XP_002327564 | Populus trichocarpa | -RRTDELVDGPNASHITPTA- | -MGIAPESQASTESVYNAALALGIANQLTNILRDVGEDARR- |
|  | BAF49052 | Prunus mume | -RRTDELVDGPNASHITPTA- | -MGISPESQATTESVYNAALALGIANQLTNILRDVGEDARR- |
|  | XP_002532975 | Ricinus communis | -RRTDELVDGPNASHITPTA- | -MGIAPESQAATESVYNAALALGIANQLTNILRDVGEDARR- |
|  | AAX19898 | Salicornia europaea | -RRTDELVDGPNASHITPTA- | -MGIAPESKAPTESVYNAALALGIANQLTNILRDVGEDSRR- |
|  | ABR57229 | S. lycopersicum PSY1 | -RRTDELVDGPNASHITPSA- | -MGIAPESKATTESVYNAALALGIANQLTNILRDVGEDARR- |
|  | ABU40771 | S. lycopersicum PSY2 | -RRTDELVDGPNASHITPQA- | -MGIAPESKATTESVYNAALALGIANQLTNILRDVGEDARR- |
|  | XP002271575 | Vitis vinifera | -RRTDELVDGPNASHITPTA- | -MGIAPESQATTESVYKAALALGIANQLTNILRDVGEDARR- |

Figure 5. Alignment of phytoene synthase amino acid sequences

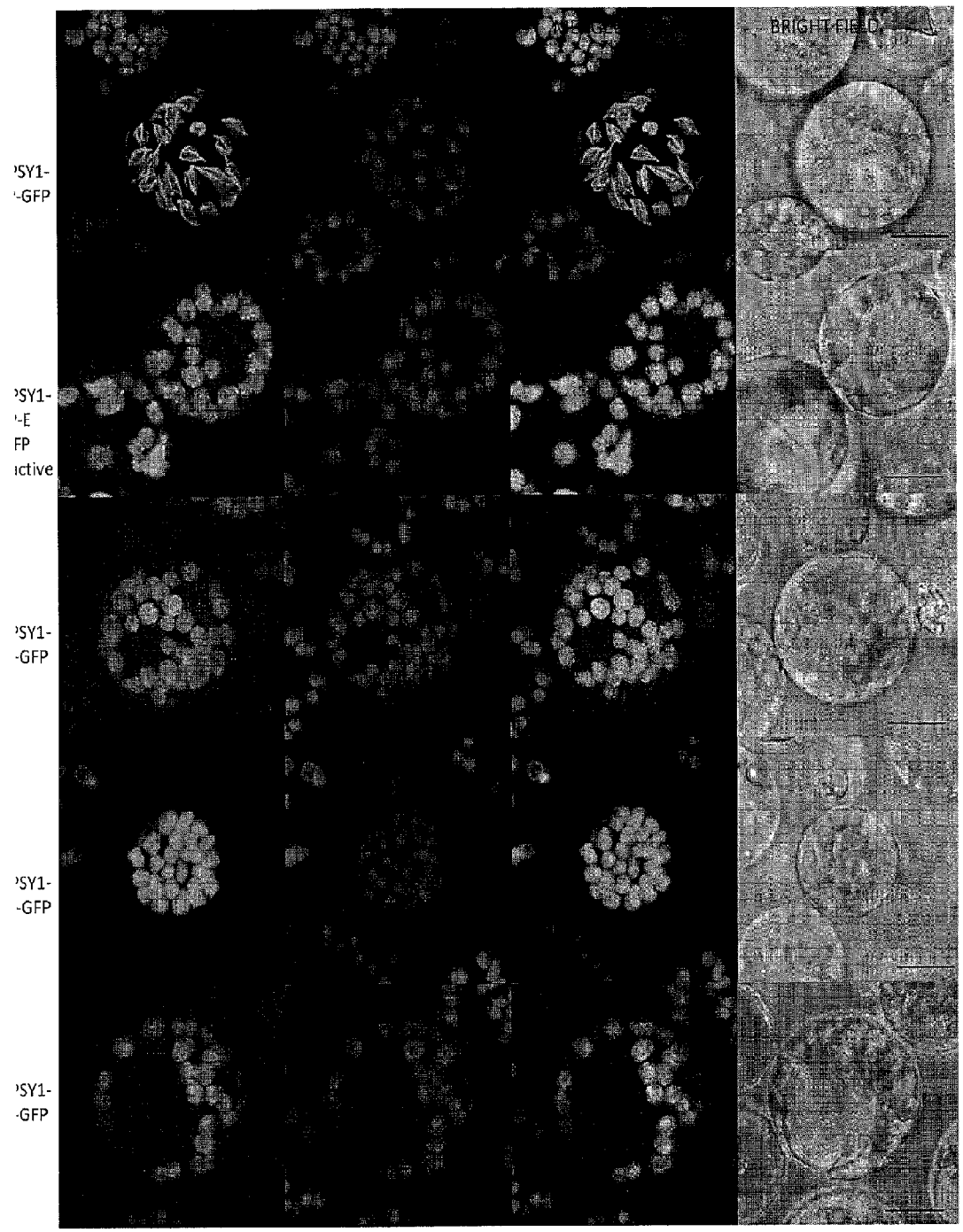
Figure 6 Transient expression of zmPSY1-NP-GFP and its mutagenized variants in etiolated maize protoplasts.

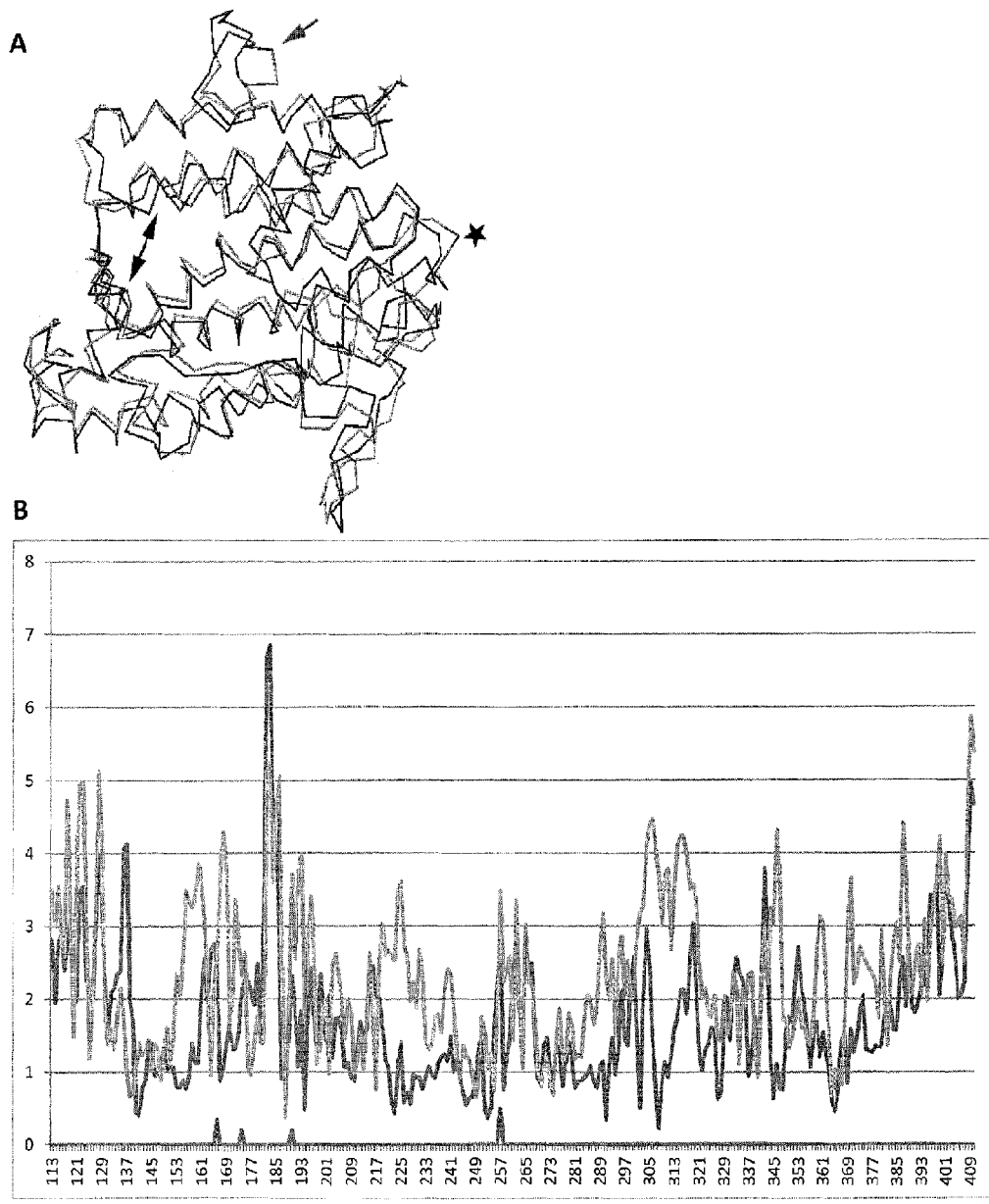
Figure 7. Sequence of zmPSY1s with transit peptide removed threaded onto crystal structure of squalene synthase

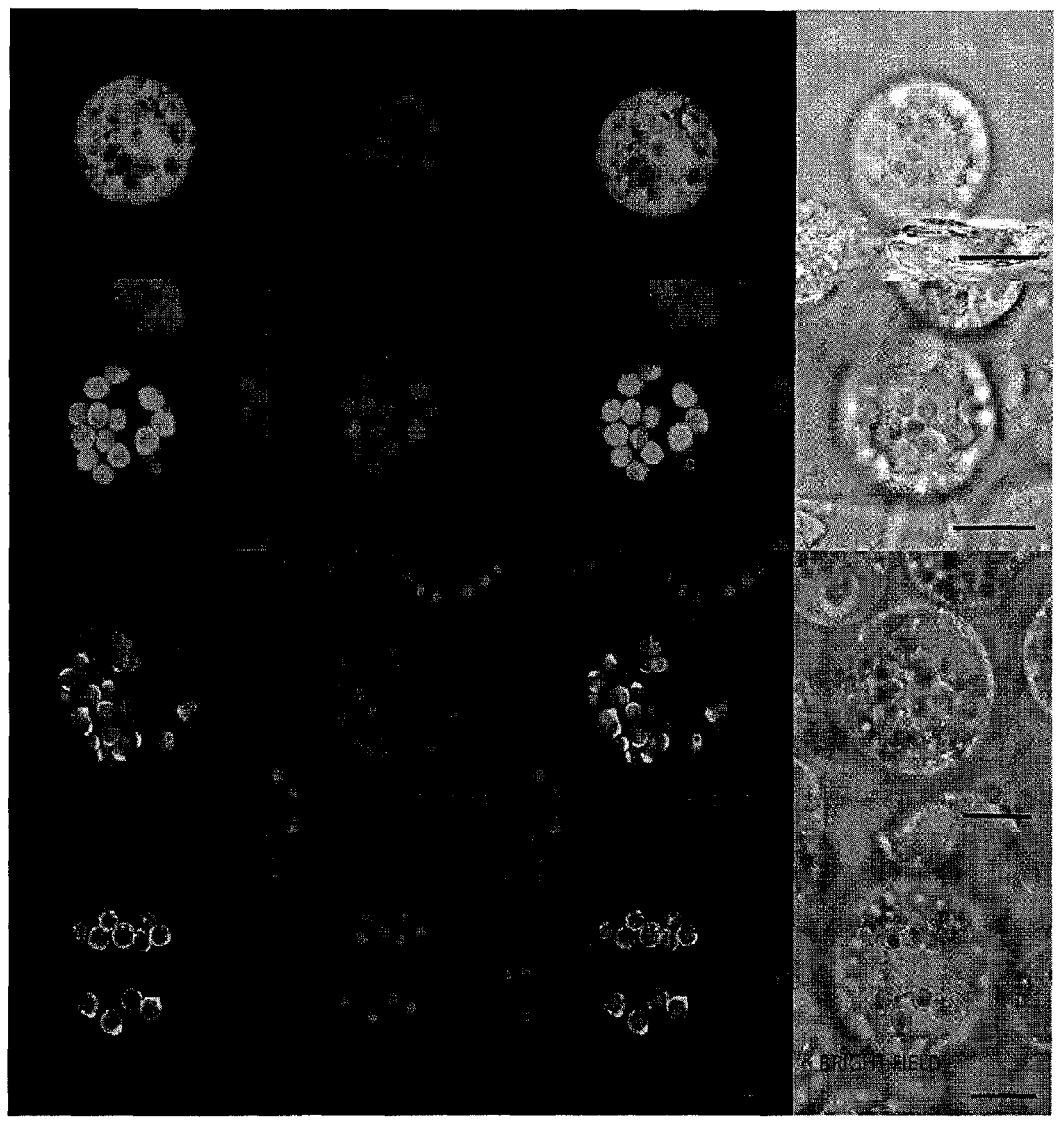
Figure 8. Overexpression of proteins with known location in etiolated maize protoplasts.

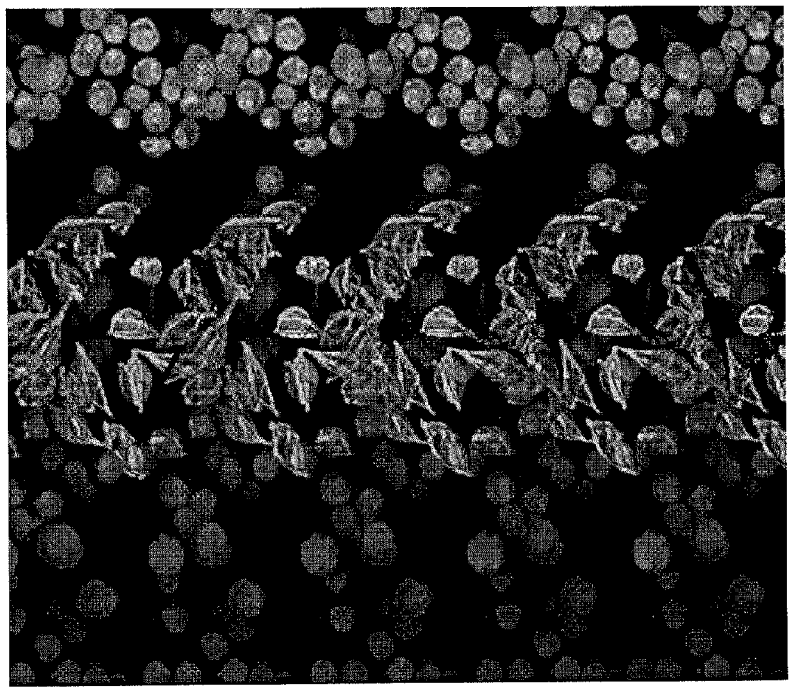
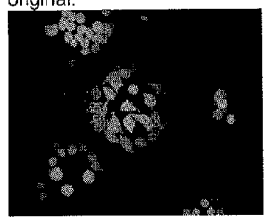
Figure 9. Hidden 3D ("third eye") stereogram of transiently expressed $_{zm}$PSY1-NP-GFP in etiolated maize protoplasts.

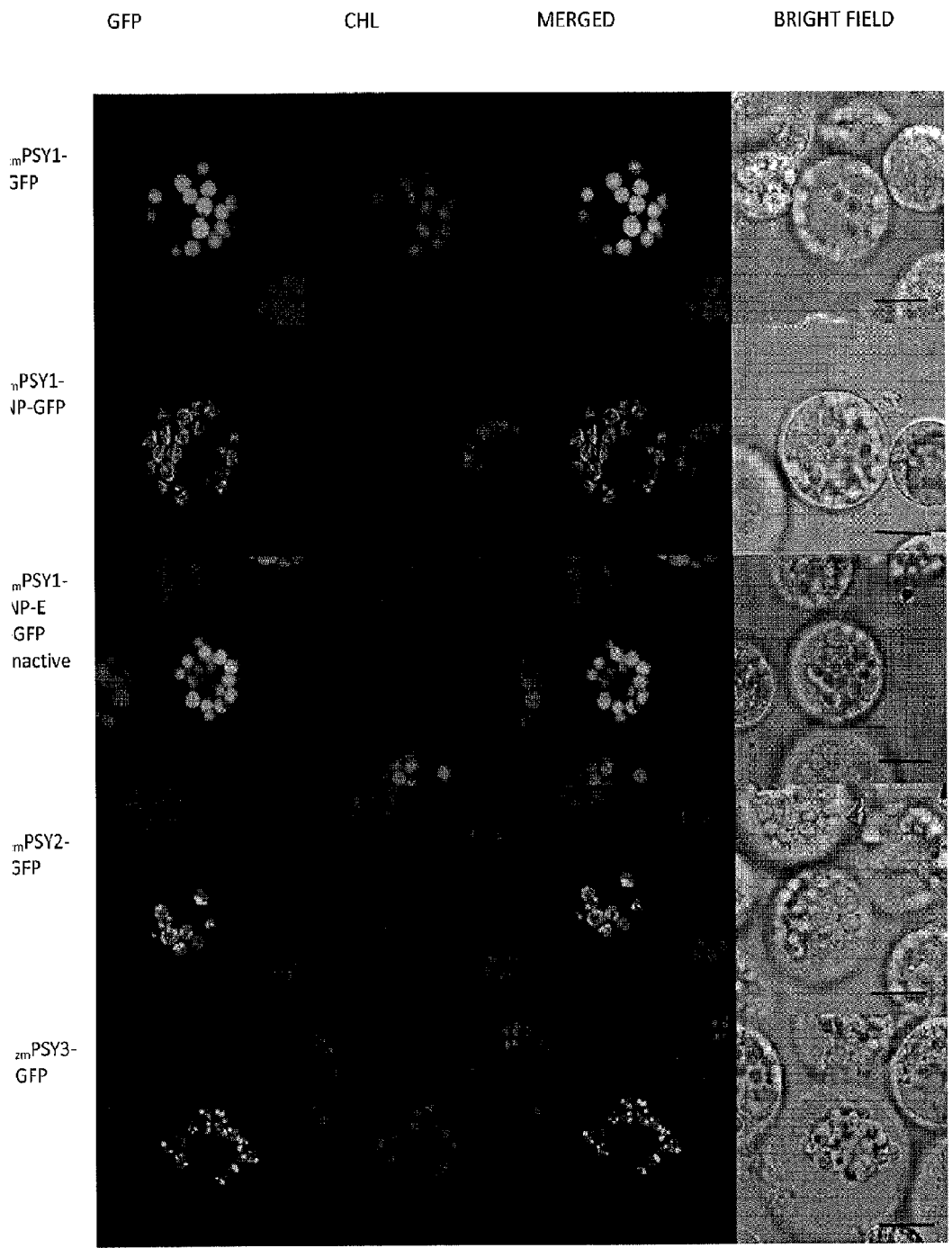
Figure 10. Transient expression of $_{zm}$PSY-GFP variants in etiolated maize protoplasts from PSY1 knockout line, *y1-8549*. The localization pattern is consistent with the one in protoplasts from standard B73 line.

Figure 11. Spectral dye separation for transiently expressed GFP-fusion proteins in maize PSY1 knockout leaf protoplasts.
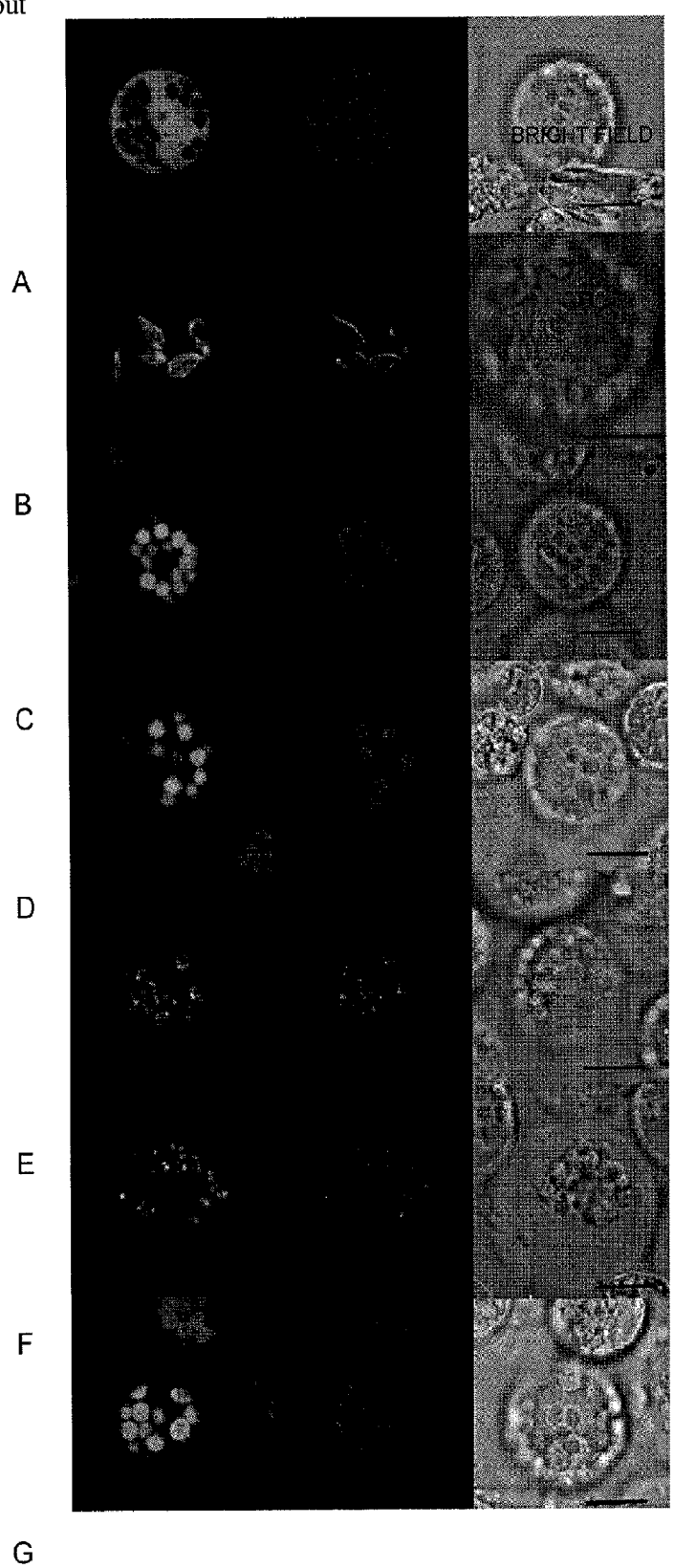

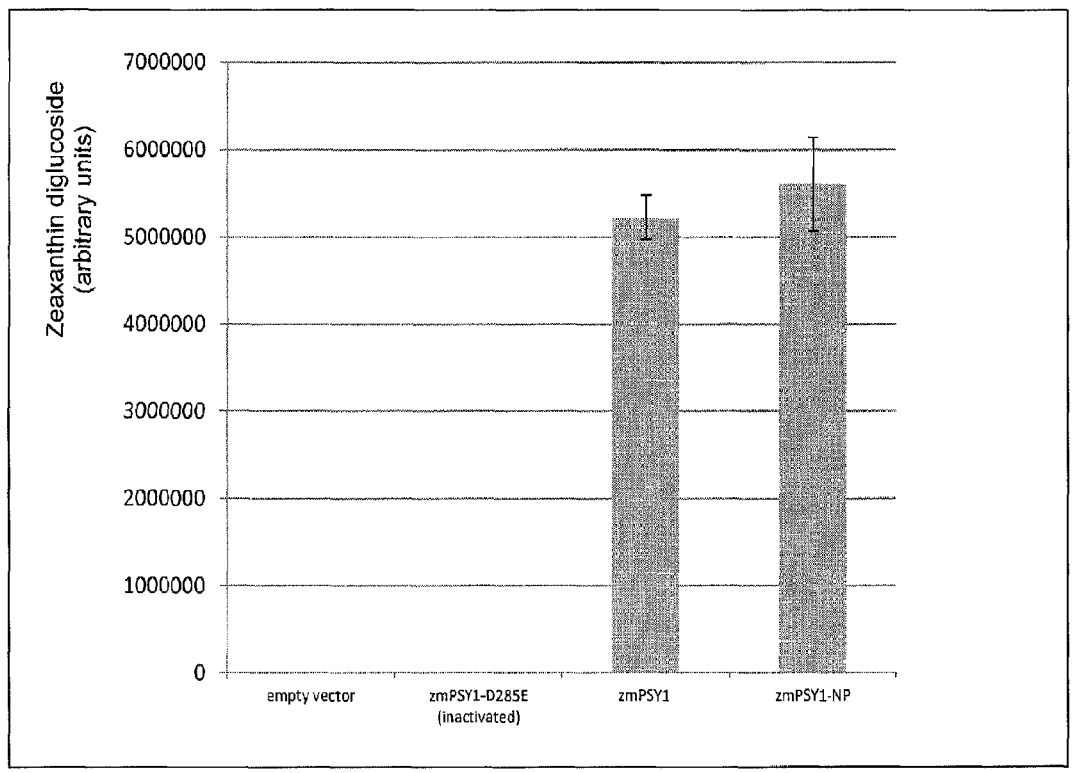
Figure 12. *E. coli* complementation test.

SEQUENCE LISTING

<160> NUMBER OF SEQ ID NOS: 145

<210> SEQ ID NO 1
<211> LENGTH: 410
<212> TYPE: PRT
<213> ORGANISM: Zea mays

<400> SEQUENCE: 1

```
Met Ala Ile Ile Leu Val Arg Ala Ala Ser Pro Gly Leu Ser Ala Ala
1               5                   10                  15

Asp Ser Ile Ser His Gln Gly Thr Leu Gln Cys Ser Thr Leu Leu Lys
            20                  25                  30

Thr Lys Arg Pro Ala Ala Arg Arg Trp Met Pro Cys Ser Leu Leu Gly
        35                  40                  45

Leu His Pro Trp Glu Ala Gly Pro Ser Pro Ala Val Tyr Ser Ser
    50                  55                  60

Leu Ala Val Asn Pro Ala Gly Glu Ala Val Ser Ser Glu Gln Lys
65                  70                  75                  80

Val Tyr Asp Val Val Leu Lys Gln Ala Ala Leu Leu Lys Arg Gln Leu
                85                  90                  95

Arg Thr Pro Val Leu Asp Ala Arg Pro Gln Asp Met Asp Met Pro Arg
            100                 105                 110

Asn Gly Leu Lys Glu Ala Tyr Asp Arg Cys Gly Glu Ile Cys Glu Glu
```

115                 120                 125

Tyr Ala Lys Thr Phe Tyr Leu Gly Thr Met Leu Met Thr Glu Glu Arg
            130                 135                 140

Arg Arg Ala Ile Trp Ala Ile Tyr Val Trp Cys Arg Arg Thr Asp Glu
145                 150                 155                 160

Leu Val Asp Gly Pro Asn Ala Asn Tyr Ile Thr Pro Thr Ala Leu Asp
                165                 170                 175

Arg Trp Glu Lys Arg Leu Glu Asp Leu Phe Thr Gly Arg Pro Tyr Asp
            180                 185                 190

Met Leu Asp Ala Ala Leu Ser Asp Thr Ile Ser Arg Phe Pro Ile Asp
        195                 200                 205

Ile Gln Pro Phe Arg Asp Met Ile Glu Gly Met Arg Ser Asp Leu Arg
    210                 215                 220

Lys Thr Arg Tyr Asn Asn Phe Asp Glu Leu Tyr Met Tyr Cys Tyr Tyr
225                 230                 235                 240

Val Ala Gly Thr Val Gly Leu Met Ser Val Pro Val Met Gly Ile Ala
                245                 250                 255

Thr Glu Ser Lys Ala Thr Thr Glu Ser Val Tyr Ser Ala Ala Leu Ala
            260                 265                 270

Leu Gly Ile Ala Asn Gln Leu Thr Asn Ile Leu Arg Asp Val Gly Glu
        275                 280                 285

Asp Ala Arg Arg Gly Arg Ile Tyr Leu Pro Gln Asp Glu Leu Ala Gln
    290                 295                 300

Ala Gly Leu Ser Asp Glu Asp Ile Phe Lys Gly Val Thr Asn Arg
305                 310                 315                 320

Trp Arg Asn Phe Met Lys Arg Gln Ile Lys Arg Ala Arg Met Phe Phe
                325                 330                 335

Glu Glu Ala Glu Arg Gly Val Thr Glu Leu Ser Gln Ala Ser Arg Trp
            340                 345                 350

Pro Val Trp Ala Ser Leu Leu Leu Tyr Arg Gln Ile Leu Asp Glu Ile
        355                 360                 365

Glu Ala Asn Asp Tyr Asn Asn Phe Thr Lys Arg Ala Tyr Val Gly Lys
    370                 375                 380

Gly Lys Lys Leu Leu Ala Leu Pro Val Ala Tyr Gly Lys Ser Leu Leu
385                 390                 395                 400

Leu Pro Cys Ser Leu Arg Asn Gly Gln Thr
                405                 410

<210> SEQ ID NO 2
<211> LENGTH: 402
<212> TYPE: PRT
<213> ORGANISM: Zea mays

<400> SEQUENCE: 2

Met Ala Ala Gly Ser Ser Ala Val Trp Ala Gln His Pro Ala Cys
1               5                   10                  15

Ser Gly Gly Lys Phe His His Leu Ser Pro Ser His Ser His Cys Arg
            20                  25                  30

Pro Arg Arg Ala Leu Gln Thr Pro Pro Ala Leu Pro Ala Arg Arg Ser
        35                  40                  45

Gly Ala Ser Pro Pro Arg Ala Ser Leu Ala Ala Ala Pro Ala Val
    50                  55                  60

Ala Val Arg Thr Ala Ser Glu Glu Ala Val Tyr Glu Val Val Leu Arg
65                  70                  75                  80

```
Gln Ala Ala Leu Val Glu Ala Thr Pro Gln Arg Arg Thr Arg
                85                  90                  95

Gln Pro Arg Trp Ala Glu Glu Glu Glu Arg Val Leu Gly Trp
            100                 105                 110

Gly Leu Leu Gly Asp Ala Tyr Asp Arg Cys Gly Glu Val Cys Ala Glu
        115                 120                 125

Tyr Ala Lys Thr Phe Tyr Leu Gly Thr Gln Leu Met Thr Pro Glu Arg
    130                 135                 140

Arg Lys Val Ala Trp Ala Ile Tyr Val Trp Cys Arg Arg Thr Asp Glu
145                 150                 155                 160

Leu Val Asp Gly Pro Asn Ala Ser Tyr Ile Thr Pro Thr Ala Leu Asp
                165                 170                 175

Arg Trp Glu Lys Arg Leu Glu Asp Leu Phe Glu Gly Arg Pro Tyr Asp
            180                 185                 190

Met Tyr Asp Ala Ala Leu Ser Asp Thr Val Ser Lys Phe Pro Val Asp
        195                 200                 205

Ile Gln Pro Phe Lys Asp Met Val Gln Gly Met Arg Leu Asp Leu Trp
    210                 215                 220

Lys Ser Arg Tyr Met Thr Phe Asp Glu Leu Tyr Leu Tyr Cys Tyr Tyr
225                 230                 235                 240

Val Ala Gly Thr Val Gly Leu Met Thr Val Pro Val Met Gly Ile Ala
                245                 250                 255

Pro Asp Ser Lys Ala Ser Thr Glu Ser Val Tyr Asn Ala Ala Leu Ala
            260                 265                 270

Leu Gly Ile Ala Asn Gln Leu Thr Asn Ile Leu Arg Asp Val Gly Glu
        275                 280                 285

Asp Ala Arg Arg Gly Arg Ile Tyr Leu Pro Leu Asp Glu Leu Ala Gln
    290                 295                 300

Ala Gly Leu Thr Glu Glu Asp Ile Phe Arg Gly Lys Val Thr Gly Lys
305                 310                 315                 320

Trp Arg Arg Phe Met Lys Gly Gln Ile Gln Arg Ala Arg Leu Phe Phe
                325                 330                 335

Asp Glu Ala Glu Lys Gly Val Thr His Leu Asp Ser Ala Ser Arg Trp
            340                 345                 350

Pro Val Leu Ala Ser Leu Trp Leu Tyr Arg Gln Ile Leu Asp Ala Ile
        355                 360                 365

Glu Ala Asn Asp Tyr Asn Asn Phe Thr Lys Arg Ala Tyr Val Gly Lys
    370                 375                 380

Ala Lys Lys Leu Leu Ser Leu Pro Leu Ala Tyr Ala Arg Ala Ala Val
385                 390                 395                 400

Ala Pro

<210> SEQ ID NO 3
<211> LENGTH: 426
<212> TYPE: PRT
<213> ORGANISM: Zea mays

<400> SEQUENCE: 3

Met Met Ser Thr Ser Arg Ala Val Lys Ser Pro Ala Cys Ala Ala Arg
1               5                   10                  15

Arg Arg Gln Trp Ser Ala Asp Ala Pro Asn Arg Thr Ala Thr Phe Leu
            20                  25                  30

Ala Cys Arg His Gly Arg Arg Leu Gly Gly Gly Gly Ala Pro Cys
        35                  40                  45
```

Ser Val Arg Ala Glu Gly Ser Asn Thr Ile Val Cys Leu Glu Ala Glu
 50                  55                  60

Ala Trp Gly Gly Ala Pro Ala Leu Pro Gly Leu Arg Val Ala Ala Pro
 65                  70                  75                  80

Ser Pro Gly Asp Ala Phe Val Val Pro Ser Glu Gln Arg Val His Glu
                 85                  90                  95

Val Val Leu Arg Gln Ala Ala Leu Ala Ala Ala Pro Arg Thr Ala
             100                 105                 110

Arg Ile Glu Pro Val Pro Leu Asp Gly Gly Leu Lys Ala Ala Phe His
             115                 120                 125

Arg Cys Gly Glu Val Cys Arg Glu Tyr Ala Lys Thr Phe Tyr Leu Ala
 130                 135                 140

Thr Gln Leu Met Thr Pro Glu Arg Arg Ile Ala Ile Trp Ala Ile Tyr
 145                 150                 155                 160

Val Trp Cys Arg Arg Thr Asp Glu Leu Val Asp Gly Pro Asn Ala Ser
                 165                 170                 175

His Ile Ser Ala Leu Ala Leu Asp Arg Trp Glu Ser Arg Leu Glu Asp
             180                 185                 190

Ile Phe Ala Gly Arg Pro Tyr Asp Met Leu Asp Ala Ala Leu Ser Asp
             195                 200                 205

Thr Val Ala Arg Phe Pro Val Asp Ile Gln Pro Phe Arg Asp Met Ile
 210                 215                 220

Glu Gly Met Arg Met Asp Leu Lys Lys Ser Arg Tyr Arg Ser Phe Asp
 225                 230                 235                 240

Glu Leu Tyr Leu Tyr Cys Tyr Tyr Val Ala Gly Thr Val Gly Leu Met
                 245                 250                 255

Ser Val Pro Val Met Gly Ile Ser Pro Ala Ser Arg Ala Ala Thr Glu
             260                 265                 270

Thr Val Tyr Lys Gly Ala Leu Ala Leu Gly Leu Ala Asn Gln Leu Thr
             275                 280                 285

Asn Ile Leu Arg Asp Val Gly Glu Asp Ala Arg Arg Gly Arg Ile Tyr
 290                 295                 300

Leu Pro Gln Asp Glu Leu Glu Met Ala Gly Leu Ser Asp Ala Asp Val
 305                 310                 315                 320

Leu Asp Gly Arg Val Thr Asp Glu Trp Arg Gly Phe Met Arg Gly Gln
                 325                 330                 335

Ile Ala Arg Ala Arg Ala Phe Phe Arg Gln Ala Glu Gly Ala Thr
             340                 345                 350

Glu Leu Asn Gln Glu Ser Arg Trp Pro Val Trp Ser Leu Leu Leu
 355                 360                 365

Tyr Arg Gln Ile Leu Asp Glu Ile Glu Ala Asn Asp Tyr Asp Asn Phe
 370                 375                 380

Thr Arg Arg Ala Tyr Val Pro Lys Thr Lys Lys Leu Met Ala Leu Pro
 385                 390                 395                 400

Lys Ala Tyr Leu Arg Ser Leu Val Val Pro Ser Ser Ser Gln Ala
                 405                 410                 415

Glu Ser Arg Arg Arg Tyr Ser Thr Leu Thr
                 420                 425

<210> SEQ ID NO 4
<211> LENGTH: 421
<212> TYPE: PRT
<213> ORGANISM: Oryza sativa

<400> SEQUENCE: 4

-continued

```
Met Ala Ala Ile Thr Leu Leu Arg Ser Ala Ser Leu Pro Gly Leu Ser
1               5                   10                  15

Asp Ala Leu Ala Arg Asp Ala Ala Val Gln His Val Cys Ser Ser
            20                  25                  30

Cys Leu Pro Ser Asn Asn Lys Glu Lys Lys Arg Arg Trp Ile Leu Cys
        35                  40                  45

Ser Leu Lys Tyr Ala Cys Leu Gly Val Asp Pro Ala Pro Gly Glu Ile
    50                  55                  60

Ala Arg Thr Ser Pro Val Tyr Ser Ser Leu Thr Val Thr Pro Ala Gly
65                  70                  75                  80

Glu Ala Val Ile Ser Ser Glu Gln Lys Val Tyr Asp Val Val Leu Lys
                85                  90                  95

Gln Ala Ala Leu Leu Lys Arg His Leu Arg Pro Gln Pro His Thr Ile
            100                 105                 110

Pro Ile Val Pro Lys Asp Leu Asp Leu Pro Arg Asn Gly Leu Lys Gln
        115                 120                 125

Ala Tyr His Arg Cys Gly Glu Ile Cys Glu Glu Tyr Ala Lys Thr Phe
    130                 135                 140

Tyr Leu Gly Thr Met Leu Met Thr Glu Asp Arg Arg Arg Ala Ile Trp
145                 150                 155                 160

Ala Ile Tyr Val Trp Cys Arg Arg Thr Asp Glu Leu Val Asp Gly Pro
                165                 170                 175

Asn Ala Ser His Ile Thr Pro Ser Ala Leu Asp Arg Trp Glu Lys Arg
            180                 185                 190

Leu Asp Asp Leu Phe Thr Gly Arg Pro Tyr Asp Met Leu Asp Ala Ala
        195                 200                 205

Leu Ser Asp Thr Ile Ser Lys Ser Pro Ile Asp Ile Gln Pro Phe Arg
    210                 215                 220

Asp Met Ile Glu Gly Met Arg Ser Asp Leu Arg Lys Thr Arg Tyr Lys
225                 230                 235                 240

Asn Phe Asp Glu Leu Tyr Met Tyr Cys Tyr Tyr Val Ala Gly Thr Val
                245                 250                 255

Gly Leu Met Ser Val Pro Val Met Gly Ile Ala Pro Glu Ser Lys Ala
            260                 265                 270

Thr Thr Glu Ser Val Tyr Ser Ala Ala Leu Ala Leu Gly Ile Ala Asn
        275                 280                 285

Gln Leu Thr Asn Ile Leu Arg Asp Val Gly Glu Asp Ala Arg Arg Gly
    290                 295                 300

Arg Ile Tyr Leu Pro Gln Asp Glu Leu Ala Glu Ala Gly Leu Ser Asp
305                 310                 315                 320

Glu Asp Ile Phe Asn Gly Val Val Thr Asn Lys Trp Arg Ser Phe Met
                325                 330                 335

Lys Arg Gln Ile Lys Arg Ala Arg Met Phe Phe Glu Glu Ala Glu Arg
            340                 345                 350

Gly Val Thr Glu Leu Ser Gln Ala Ser Arg Trp Pro Val Trp Ala Ser
        355                 360                 365

Leu Leu Leu Tyr Arg Gln Ile Leu Asp Glu Ile Glu Ala Asn Asp Tyr
    370                 375                 380

Asn Asn Phe Thr Lys Arg Thr Tyr Val Gly Lys Ala Lys Lys Leu Leu
385                 390                 395                 400

Ala Leu Pro Val Ala Tyr Gly Arg Ser Leu Leu Met Pro Tyr Ser Leu
                405                 410                 415
```

Arg Asn Ser Gln Lys
            420

<210> SEQ ID NO 5
<211> LENGTH: 397
<212> TYPE: PRT
<213> ORGANISM: Oryza sativa

<400> SEQUENCE: 5

Met Ala Ser Ser Ser Ala Ala Leu Trp Thr Ala Ala Pro His
1               5                   10                  15

Pro His Gly Ser Cys Ile Arg Ile His Ala Ile Phe His Gln Arg His
            20                  25                  30

Gln Arg Arg Gly Arg Arg Pro Val Val Ala Ser Ser Val Arg Pro
        35                  40                  45

Leu Gln Ala Ala Ser Leu Ala Val Ala Thr Ala Pro Val Ala Val Ala
    50                  55                  60

Ser Arg Arg Thr Ala Ala Glu Glu Ala Val Tyr Glu Val Val Leu Arg
65                  70                  75                  80

Gln Ala Ala Leu Glu Glu Ala Thr His Arg Arg Gly Ala Gly Ala Pro
                85                  90                  95

Arg Trp Ala Glu Glu Asp Ala Val Asp Trp Gly Leu Leu Gly Asp
            100                 105                 110

Ala Tyr His Arg Cys Gly Glu Val Cys Ala Glu Tyr Ala Lys Thr Phe
        115                 120                 125

Tyr Leu Gly Thr Gln Leu Met Thr Pro Glu Arg Arg Lys Ala Val Trp
    130                 135                 140

Ala Ile Tyr Val Trp Cys Arg Arg Thr Asp Glu Leu Val Asp Gly Pro
145                 150                 155                 160

Asn Ser Ser Tyr Ile Thr Pro Lys Ala Leu Asp Arg Trp Glu Lys Arg
                165                 170                 175

Leu Glu Asp Leu Phe Glu Gly Arg Pro Tyr Asp Met Tyr Asp Ala Ala
            180                 185                 190

Leu Ser Asp Thr Val Ser Lys Phe Pro Val Asp Ile Gln Pro Phe Lys
        195                 200                 205

Asp Met Ile Glu Gly Met Arg Leu Asp Leu Trp Lys Ser Arg Tyr Arg
    210                 215                 220

Ser Phe Asp Glu Leu Tyr Leu Tyr Cys Tyr Tyr Val Ala Gly Thr Val
225                 230                 235                 240

Gly Leu Met Thr Val Pro Val Met Gly Ile Ala Pro Asp Ser Lys Ala
                245                 250                 255

Ser Thr Glu Ser Val Tyr Asn Ala Ala Leu Ala Leu Gly Ile Ala Asn
            260                 265                 270

Gln Leu Thr Asn Ile Leu Arg Asp Val Gly Glu Asp Ser Arg Arg Gly
        275                 280                 285

Arg Ile Tyr Leu Pro Leu Asp Glu Leu Ala Glu Ala Gly Leu Thr Glu
    290                 295                 300

Glu Asp Ile Phe Arg Gly Lys Val Thr Asp Lys Trp Arg Lys Phe Met
305                 310                 315                 320

Lys Gly Gln Ile Leu Arg Ala Arg Leu Phe Phe Asp Glu Ala Glu Lys
                325                 330                 335

Gly Val Ala His Leu Asp Ser Ala Ser Arg Trp Pro Val Leu Ala Ser
            340                 345                 350

Leu Trp Leu Tyr Arg Gln Ile Leu Asp Ala Ile Glu Ala Asn Asp Tyr
        355                 360                 365

Asn Asn Phe Thr Lys Arg Ala Tyr Val Asn Ala Lys Lys Leu Leu
            370                 375                 380

Ser Leu Pro Val Ala Tyr Ala Arg Ala Ala Val Ala Ser
385                 390                 395

<210> SEQ ID NO 6
<211> LENGTH: 422
<212> TYPE: PRT
<213> ORGANISM: Arabidopsis thaliana

<400> SEQUENCE: 6

Met Ser Ser Val Ala Val Leu Trp Val Thr Ser Ser Leu Asn
1               5                   10                  15

Pro Asp Pro Met Asn Asn Cys Gly Leu Val Arg Val Leu Glu Ser Ser
                20                  25                  30

Arg Leu Phe Ser Pro Cys Gln Asn Gln Arg Leu Asn Lys Gly Lys Lys
            35                  40                  45

Lys Gln Ile Pro Thr Trp Ser Ser Phe Val Arg Asn Arg Ser Arg
    50                  55                  60

Arg Ile Gly Val Val Ser Ser Leu Val Ala Ser Pro Ser Gly Glu
65                  70                  75                  80

Ile Ala Leu Ser Ser Glu Glu Lys Val Tyr Asn Val Leu Lys Gln
                85                  90                  95

Ala Ala Leu Val Asn Lys Gln Leu Arg Ser Ser Ser Tyr Asp Leu Asp
            100                 105                 110

Val Lys Lys Pro Gln Asp Val Val Leu Pro Gly Ser Leu Ser Leu Leu
        115                 120                 125

Gly Glu Ala Tyr Asp Arg Cys Gly Glu Val Cys Ala Glu Tyr Ala Lys
130                 135                 140

Thr Phe Tyr Leu Gly Thr Leu Leu Met Thr Pro Glu Arg Arg Lys Ala
145                 150                 155                 160

Ile Trp Ala Ile Tyr Val Trp Cys Arg Arg Thr Asp Glu Leu Val Asp
                165                 170                 175

Gly Pro Asn Ala Ser His Ile Thr Pro Met Ala Leu Asp Arg Trp Glu
            180                 185                 190

Ala Arg Leu Glu Asp Leu Phe Arg Gly Arg Pro Phe Asp Met Leu Asp
        195                 200                 205

Ala Ala Leu Ala Asp Thr Val Ala Arg Tyr Pro Val Asp Ile Gln Pro
    210                 215                 220

Phe Arg Asp Met Ile Glu Gly Met Arg Met Asp Leu Lys Lys Ser Arg
225                 230                 235                 240

Tyr Gln Asn Phe Asp Asp Leu Tyr Leu Tyr Cys Tyr Tyr Val Ala Gly
                245                 250                 255

Thr Val Gly Leu Met Ser Val Pro Val Met Gly Ile Asp Pro Lys Ser
            260                 265                 270

Lys Ala Thr Thr Glu Ser Val Tyr Asn Ala Ala Leu Ala Leu Gly Ile
        275                 280                 285

Ala Asn Gln Leu Thr Asn Ile Leu Arg Asp Val Gly Glu Asp Ala Arg
    290                 295                 300

Arg Gly Arg Val Tyr Leu Pro Gln Asp Glu Leu Ala Gln Ala Gly Leu
305                 310                 315                 320

Ser Asp Glu Asp Ile Phe Ala Gly Lys Val Thr Asp Lys Trp Arg Asn
                325                 330                 335

Phe Met Lys Met Gln Leu Lys Arg Ala Arg Met Phe Phe Asp Glu Ala

```
                340                 345                 350
Glu Lys Gly Val Thr Glu Leu Ser Ala Ala Ser Arg Trp Pro Val Trp
            355                 360                 365

Ala Ser Leu Leu Leu Tyr Arg Arg Ile Leu Asp Glu Ile Glu Ala Asn
        370                 375                 380

Asp Tyr Asn Asn Phe Thr Lys Arg Ala Tyr Val Gly Lys Val Lys Lys
385                 390                 395                 400

Ile Ala Ala Leu Pro Leu Ala Tyr Ala Lys Ser Val Leu Lys Thr Ser
                405                 410                 415

Ser Ser Arg Leu Ser Ile
            420

<210> SEQ ID NO 7
<211> LENGTH: 342
<212> TYPE: PRT
<213> ORGANISM: Homo sapiens

<400> SEQUENCE: 7

Met Glu Phe Val Lys Cys Leu Gly His Pro Glu Glu Phe Tyr Asn Leu
1               5                   10                  15

Val Arg Phe Arg Ile Gly Gly Lys Arg Lys Val Met Pro Lys Met Asp
            20                  25                  30

Gln Asp Ser Leu Ser Ser Ser Leu Lys Thr Cys Tyr Lys Tyr Leu Asn
        35                  40                  45

Gln Thr Ser Arg Ser Phe Ala Ala Val Ile Gln Ala Leu Asp Gly Glu
    50                  55                  60

Met Arg Asn Ala Val Cys Ile Phe Tyr Leu Val Leu Arg Ala Leu Asp
65                  70                  75                  80

Thr Leu Glu Asp Asp Met Thr Ile Val Glu Lys Lys Val Pro Leu Leu
                85                  90                  95

His Asn Phe His Ser Phe Leu Tyr Gln Pro Asp Trp Arg Phe Met Asp
            100                 105                 110

Arg Gln Val Leu Glu Asp Phe Pro Thr Ile Ser Leu Glu Phe Arg Asn
        115                 120                 125

Leu Ala Glu Lys Tyr Gln Arg Met Gly Ile Gly Met Ala Glu Phe Leu
    130                 135                 140

Asp Lys His Val Thr Ser Glu Gln Glu Trp Asp Lys Tyr Cys His Tyr
145                 150                 155                 160

Val Ala Gly Leu Val Gly Ile Gly Leu Ser Arg Leu Phe Ser Ala Ser
                165                 170                 175

Glu Phe Glu Asp Pro Leu Val Gly Glu Asp Thr Glu Arg Ala Asn Ser
            180                 185                 190

Met Gly Leu Phe Leu Gln Lys Thr Asn Ile Ile Arg Asp Tyr Leu Glu
        195                 200                 205

Asp Gln Gln Gly Gly Arg Glu Phe Trp Pro Gln Glu Val Trp Ser Arg
    210                 215                 220

Tyr Val Lys Lys Leu Gly Asp Phe Ala Lys Pro Glu Asn Ile Asp Leu
225                 230                 235                 240

Ala Val Gln Cys Leu Asn Glu Leu Ile Thr Asn Ala Leu His His Ile
                245                 250                 255

Pro Asp Val Ile Thr Tyr Leu Ser Arg Leu Arg Asn Gln Ser Val Phe
            260                 265                 270

Asn Phe Cys Ala Ile Pro Gln Val Met Ala Ile Ala Thr Leu Ala Ala
        275                 280                 285
```

-continued

Cys Tyr Asn Asn Gln Gln Val Phe Lys Gly Ala Val Lys Ile Arg Lys
    290                 295                 300

Gly Gln Ala Val Thr Leu Met Met Asp Ala Thr Asn Met Pro Ala Val
305                 310                 315                 320

Lys Ala Ile Ile Tyr Gln Tyr Met Glu Glu Ile Tyr His Arg Ile Pro
                325                 330                 335

Asp Ser Asp Pro Ser Ser
            340

<210> SEQ ID NO 8
<211> LENGTH: 19
<212> TYPE: PRT
<213> ORGANISM: Zea mays

<400> SEQUENCE: 8

Arg Arg Thr Asp Glu Leu Val Asp Gly Pro Asn Ala Asn Tyr Ile Thr
1               5                   10                  15

Pro Thr Ala

<210> SEQ ID NO 9
<211> LENGTH: 19
<212> TYPE: PRT
<213> ORGANISM: Zea mays

<400> SEQUENCE: 9

Arg Arg Thr Asp Glu Leu Val Asp Gly Pro Asn Ala Asn Tyr Ile Thr
1               5                   10                  15

Pro Thr Ala

<210> SEQ ID NO 10
<211> LENGTH: 19
<212> TYPE: PRT
<213> ORGANISM: Zea mays

<400> SEQUENCE: 10

Arg Arg Thr Asp Glu Leu Val Asp Gly Pro Asn Ala Asn Tyr Ile Thr
1               5                   10                  15

Pro Thr Ala

<210> SEQ ID NO 11
<211> LENGTH: 19
<212> TYPE: PRT
<213> ORGANISM: Zea mays

<400> SEQUENCE: 11

Arg Arg Thr Asp Glu Leu Val Asp Gly Pro Asn Ala Asn Tyr Ile Thr
1               5                   10                  15

Pro Thr Ala

<210> SEQ ID NO 12
<211> LENGTH: 19
<212> TYPE: PRT
<213> ORGANISM: Zea mays

<400> SEQUENCE: 12

Arg Arg Thr Asp Glu Leu Val Asp Gly Pro Asn Ala Asn Tyr Ile Thr
1               5                   10                  15

Pro Thr Ala

<210> SEQ ID NO 13

```
<211> LENGTH: 19
<212> TYPE: PRT
<213> ORGANISM: Zea mays

<400> SEQUENCE: 13

Arg Arg Thr Asp Glu Leu Val Asp Gly Pro Asn Ala Asn Tyr Ile Thr
1               5                   10                  15

Pro Thr Ala

<210> SEQ ID NO 14
<211> LENGTH: 19
<212> TYPE: PRT
<213> ORGANISM: Zea diploperennis

<400> SEQUENCE: 14

Arg Arg Thr Asp Glu Leu Val Asp Gly Pro Asn Ala Asn Tyr Ile Thr
1               5                   10                  15

Pro Thr Ala

<210> SEQ ID NO 15
<211> LENGTH: 19
<212> TYPE: PRT
<213> ORGANISM: Zea luxurians

<400> SEQUENCE: 15

Arg Arg Thr Asp Glu Leu Val Asp Gly Pro Asn Ala Asn Tyr Ile Thr
1               5                   10                  15

Pro Thr Ala

<210> SEQ ID NO 16
<211> LENGTH: 19
<212> TYPE: PRT
<213> ORGANISM: Zea mays

<400> SEQUENCE: 16

Arg Arg Thr Asp Glu Leu Val Asp Gly Pro Asn Ala Asn Tyr Ile Thr
1               5                   10                  15

Pro Thr Ala

<210> SEQ ID NO 17
<211> LENGTH: 19
<212> TYPE: PRT
<213> ORGANISM: Aegilops tauschii

<400> SEQUENCE: 17

Arg Arg Thr Asp Glu Leu Val Asp Gly Pro Asn Ala Ser His Ile Thr
1               5                   10                  15

Pro Gln Ala

<210> SEQ ID NO 18
<211> LENGTH: 19
<212> TYPE: PRT
<213> ORGANISM: Coix lacryma-jobi

<400> SEQUENCE: 18

Arg Arg Thr Asp Glu Leu Val Asp Gly Pro Asn Ala Asn Tyr Ile Thr
1               5                   10                  15

Pro Thr Ala

<210> SEQ ID NO 19
<211> LENGTH: 19
```

```
<212> TYPE: PRT
<213> ORGANISM: Narcissus pseudonarcissus

<400> SEQUENCE: 19

Arg Arg Thr Asp Glu Leu Val Asp Gly His Asn Ala Ser His Ile Thr
1               5                   10                  15

Pro Ser Ala

<210> SEQ ID NO 20
<211> LENGTH: 19
<212> TYPE: PRT
<213> ORGANISM: Narcissus tazetta

<400> SEQUENCE: 20

Arg Arg Thr Asp Glu Leu Val Asp Gly His Asn Ala Ser His Ile Thr
1               5                   10                  15

Pro Ser Ala

<210> SEQ ID NO 21
<211> LENGTH: 19
<212> TYPE: PRT
<213> ORGANISM: Sorghum bicolor

<400> SEQUENCE: 21

Arg Arg Thr Asp Glu Leu Val Asp Gly Pro Asn Ala Asn Tyr Ile Thr
1               5                   10                  15

Pro Thr Ala

<210> SEQ ID NO 22
<211> LENGTH: 19
<212> TYPE: PRT
<213> ORGANISM: Sorghum bicolor

<400> SEQUENCE: 22

Arg Arg Thr Asp Glu Leu Val Asp Gly Pro Asn Ala Ser His Ile Ser
1               5                   10                  15

Ala Val Ala

<210> SEQ ID NO 23
<211> LENGTH: 19
<212> TYPE: PRT
<213> ORGANISM: Sorghum bicolor

<400> SEQUENCE: 23

Arg Arg Thr Asp Glu Leu Val Asp Gly Pro Asn Ala Ser His Ile Ser
1               5                   10                  15

Ala Val Ala

<210> SEQ ID NO 24
<211> LENGTH: 19
<212> TYPE: PRT
<213> ORGANISM: Tripsacum sp.

<400> SEQUENCE: 24

Arg Arg Thr Asp Glu Leu Val Asp Gly Pro Asn Ala Asn Tyr Ile Thr
1               5                   10                  15

Pro Thr Ala

<210> SEQ ID NO 25
<211> LENGTH: 19
<212> TYPE: PRT
```

<213> ORGANISM: Triticum aestivum

<400> SEQUENCE: 25

Arg Arg Thr Asp Glu Leu Val Asp Gly Pro Asn Ala Ser His Ile Thr
1               5                   10                  15

Pro Gln Ala

<210> SEQ ID NO 26
<211> LENGTH: 19
<212> TYPE: PRT
<213> ORGANISM: Thinopyrum ponticum

<400> SEQUENCE: 26

Arg Arg Thr Asp Glu Leu Val Asp Gly Pro Asn Ala Ser His Ile Thr
1               5                   10                  15

Pro Gln Ala

<210> SEQ ID NO 27
<211> LENGTH: 19
<212> TYPE: PRT
<213> ORGANISM: Actinidia deliciosa

<400> SEQUENCE: 27

Arg Arg Thr Asp Glu Leu Val Asp Gly Pro Asn Ala Ser His Ile Thr
1               5                   10                  15

Pro Thr Ala

<210> SEQ ID NO 28
<211> LENGTH: 19
<212> TYPE: PRT
<213> ORGANISM: Brassica rapa

<400> SEQUENCE: 28

Arg Arg Thr Asp Glu Leu Val Asp Gly Pro Asn Ala Ser His Ile Thr
1               5                   10                  15

Pro Met Ala

<210> SEQ ID NO 29
<211> LENGTH: 19
<212> TYPE: PRT
<213> ORGANISM: Carica papaya

<400> SEQUENCE: 29

Arg Arg Thr Glu Glu Leu Val Asp Gly Pro Asn Ala Ser His Ile Thr
1               5                   10                  15

Pro Thr Ala

<210> SEQ ID NO 30
<211> LENGTH: 19
<212> TYPE: PRT
<213> ORGANISM: Coffea canephora

<400> SEQUENCE: 30

Arg Arg Thr Asp Glu Leu Val Asp Gly Pro Asn Ala Ser His Ile Thr
1               5                   10                  15

Pro Thr Ala

<210> SEQ ID NO 31
<211> LENGTH: 19
<212> TYPE: PRT
<213> ORGANISM: Citrus maxima

```
<400> SEQUENCE: 31

Arg Arg Thr Asp Glu Leu Val Asp Gly Pro Asn Ala Ser Tyr Ile Thr
1               5                   10                  15

Pro Ala Ala

<210> SEQ ID NO 32
<211> LENGTH: 19
<212> TYPE: PRT
<213> ORGANISM: Citrus unshiu

<400> SEQUENCE: 32

Arg Arg Thr Asp Glu Leu Val Asp Gly Pro Asn Ala Ser His Ile Thr
1               5                   10                  15

Pro Thr Ala

<210> SEQ ID NO 33
<211> LENGTH: 19
<212> TYPE: PRT
<213> ORGANISM: Citrofortunella mitis

<400> SEQUENCE: 33

Arg Arg Thr Asp Glu Leu Val Asp Gly Pro Asn Ala Ser His Ile Thr
1               5                   10                  15

Pro Ala Ala

<210> SEQ ID NO 34
<211> LENGTH: 19
<212> TYPE: PRT
<213> ORGANISM: Cucumis melo

<400> SEQUENCE: 34

Arg Arg Thr Asp Glu Leu Val Asp Gly Pro Asn Ala Ser His Ile Thr
1               5                   10                  15

Pro Thr Ala

<210> SEQ ID NO 35
<211> LENGTH: 19
<212> TYPE: PRT
<213> ORGANISM: Daucus carota

<400> SEQUENCE: 35

Arg Arg Thr Asp Glu Leu Val Asp Gly Pro Asn Ala Ser His Ile Thr
1               5                   10                  15

Pro Gln Ala

<210> SEQ ID NO 36
<211> LENGTH: 19
<212> TYPE: PRT
<213> ORGANISM: Diospyros kaki

<400> SEQUENCE: 36

Arg Arg Thr Asp Glu Leu Val Asp Gly His Asn Ala Ser His Ile Thr
1               5                   10                  15

Pro Thr Ala

<210> SEQ ID NO 37
<211> LENGTH: 19
<212> TYPE: PRT
<213> ORGANISM: Elaeagnus umbellata
```

```
<400> SEQUENCE: 37

Arg Arg Thr Asp Glu Leu Val Asp Gly Pro Asn Ala Ser His Ile Thr
1               5                   10                  15

Pro Lys Ala

<210> SEQ ID NO 38
<211> LENGTH: 19
<212> TYPE: PRT
<213> ORGANISM: Ipomoea sp.

<400> SEQUENCE: 38

Arg Arg Thr Asp Glu Leu Val Asp Gly Pro Asn Ala Ser His Ile Thr
1               5                   10                  15

Pro Thr Ala

<210> SEQ ID NO 39
<211> LENGTH: 19
<212> TYPE: PRT
<213> ORGANISM: Manihot esculenta

<400> SEQUENCE: 39

Arg Arg Thr Asp Glu Leu Val Asp Gly Pro Asn Ala Ser His Ile Thr
1               5                   10                  15

Pro Thr Ala

<210> SEQ ID NO 40
<211> LENGTH: 19
<212> TYPE: PRT
<213> ORGANISM: Manihot esculenta

<400> SEQUENCE: 40

Arg Arg Thr Asp Glu Leu Val Asp Gly Pro Asn Ala Ser His Ile Thr
1               5                   10                  15

Pro Thr Ala

<210> SEQ ID NO 41
<211> LENGTH: 19
<212> TYPE: PRT
<213> ORGANISM: Momordica charantia

<400> SEQUENCE: 41

Arg Arg Thr Asp Glu Leu Val Asp Gly Pro Asn Ala Ser His Ile Thr
1               5                   10                  15

Pro Thr Ala

<210> SEQ ID NO 42
<211> LENGTH: 19
<212> TYPE: PRT
<213> ORGANISM: Nicotiana tabacum

<400> SEQUENCE: 42

Arg Arg Thr Asp Glu Leu Val Asp Gly Pro Asn Ala Ser His Ile Thr
1               5                   10                  15

Pro Gln Ala

<210> SEQ ID NO 43
<211> LENGTH: 19
<212> TYPE: PRT
<213> ORGANISM: Oncidium sp.

<400> SEQUENCE: 43
```

-continued

Arg Arg Thr Asp Glu Leu Val Asp Gly Pro Asn Ala Ser His Ile Thr
1               5                   10                  15

Pro Ser Ala

<210> SEQ ID NO 44
<211> LENGTH: 19
<212> TYPE: PRT
<213> ORGANISM: Populus trichocarpa

<400> SEQUENCE: 44

Arg Arg Thr Asp Glu Leu Val Asp Gly Pro Asn Ala Ser His Ile Thr
1               5                   10                  15

Pro Thr Ala

<210> SEQ ID NO 45
<211> LENGTH: 19
<212> TYPE: PRT
<213> ORGANISM: Prunus mume

<400> SEQUENCE: 45

Arg Arg Thr Asp Glu Leu Val Asp Gly Pro Asn Ala Ser His Ile Thr
1               5                   10                  15

Pro Thr Ala

<210> SEQ ID NO 46
<211> LENGTH: 19
<212> TYPE: PRT
<213> ORGANISM: Ricinus communis

<400> SEQUENCE: 46

Arg Arg Thr Asp Glu Leu Val Asp Gly Pro Asn Ala Ser His Ile Thr
1               5                   10                  15

Pro Thr Ala

<210> SEQ ID NO 47
<211> LENGTH: 19
<212> TYPE: PRT
<213> ORGANISM: Salicornia europaea

<400> SEQUENCE: 47

Arg Arg Thr Asp Glu Leu Val Asp Gly Pro Asn Ala Ser His Ile Thr
1               5                   10                  15

Pro Thr Ala

<210> SEQ ID NO 48
<211> LENGTH: 19
<212> TYPE: PRT
<213> ORGANISM: Solanum lycopersicum

<400> SEQUENCE: 48

Arg Arg Thr Asp Glu Leu Val Asp Gly Pro Asn Ala Ser His Ile Thr
1               5                   10                  15

Pro Ser Ala

<210> SEQ ID NO 49
<211> LENGTH: 19
<212> TYPE: PRT
<213> ORGANISM: Solanum lycopersicum

<400> SEQUENCE: 49

Arg Arg Thr Asp Glu Leu Val Asp Gly Pro Asn Ala Ser His Ile Thr
1               5                   10                  15

Pro Gln Ala

<210> SEQ ID NO 50
<211> LENGTH: 19
<212> TYPE: PRT
<213> ORGANISM: Vitis vinifera

<400> SEQUENCE: 50

Arg Arg Thr Asp Glu Leu Val Asp Gly Pro Asn Ala Ser His Ile Thr
1               5                   10                  15

Pro Thr Ala

<210> SEQ ID NO 51
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tctcgagatg gccatcatac tcgtacgag                                    29

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
atctagacta ggtctggcca tttctcaatg                                   30

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
actcgagaat ggctgcgggc tcgtccg                                      27

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gatgtgatct acggatggtt cat                                          23

<210> SEQ ID NO 55
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aagaattcgc caccatgatg tctacgagc                              29

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aagcggccgc ctatgttagg gtggaatagc                             30

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttctagaatg gccatcatac tcgtacgag                              29

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aggatccggt ctggccattt ctcaatgaa                              29

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atctagaatg gctgcgggct cgtcc                                  25

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aggatcctgg tgcaaccgca gcccttgca                              29

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

-continued atctctagaa tgatgtctac gagccgcgcg gtgaagtcg                         39

<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atcggatcct gttagggtgg aatagcgtct ccggctc                           37

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atctagaatg gcccatcacg ctcctac                                      27

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aagatctctt ctggctattt ctcagtgag                                    29

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aactagttcc acacgaacac acaaccccaa                                   30

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aagatcttga tgcaactgcc gctcttgcat a                                 31

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atctctagaa tggccgcttc atcc                                          24

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
atcggatccc tttccgggaa caaagttggt agc                                 33

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atcgaattca tgtcttcttc tgtagcagtg                                    30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
attggatccg tatcgatagt cttgaacttg                                    30

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
atcgaattca tggcgtcctc cgcgttcctc aacg                               34

<210> SEQ ID NO 72
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atctgatcag gtatagaaga gtacttccc                                     29

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cctgtgatgg gcatcgcacc cgagtctaaa g                                  31

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ctttagactc gggtgcgatg cccatcacag g               31

<210> SEQ ID NO 75
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
cctgtgatgg gcatcgcacc cgagtctaaa g               31

<210> SEQ ID NO 76
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ctttagactc gggtgcgatg cccatcacag g               31

<210> SEQ ID NO 77
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
gatgggccaa acgccagcta cattacacca acag            34

<210> SEQ ID NO 78
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
ctgttggtgt aatgtagctg gcgtttggcc catc            34

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
cctgtgatgg gcatcgcatc cgagtctaaa g               31

<210> SEQ ID NO 80
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ctttagactc ggatgcgatg cccatcacag g                           31

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gatgggccaa acgccagcta cattacacca acag                        34

<210> SEQ ID NO 82
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctgttggtgt aatgtagctg gcgtttggcc catc                        34

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cctgtcatgg gcatcgctac cgactccaa                              29

<210> SEQ ID NO 84
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ttggagtcgg tagcgatgcc catgacagg                              29

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cctgtcatgg gcatcgctac cgactccaa                              29

```
<210> SEQ ID NO 86
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttggagtcgg tagcgatgcc catgacagg                                          29

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gacggtccca acgcgaacta catcacgccg ac                                      32

<210> SEQ ID NO 88
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtcggcgtga tgtagttcgc gttgggaccg tc                                      32

<210> SEQ ID NO 89
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gacggtccca acgcgaacta catcacgccg ac                                      32

<210> SEQ ID NO 90
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gtcggcgtga tgtagttcgc gttgggaccg tc                                      32

<210> SEQ ID NO 91
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gttcctgtga tgggtattgc aaccgagtcg aag                                     33

<210> SEQ ID NO 92
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
cttcgactcg gttgcaatac ccatcacagg aac                                33

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cctgtgatgg gcatcgcacc cgagtctaaa g                                  31

<210> SEQ ID NO 94
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ctttagactc gggtgcgatg cccatcacag g                                  31

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgaacatact ccgggaggtt ggagaggatg cta                                33

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tagcatcctc tccaacctcc cggagtatgt tcg                                33

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
cgaacatact ccgggaggtt ggagaggatg cta                                33

<210> SEQ ID NO 98
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tagcatcctc tccaacctcc cggagtatgt tcg                                    33

<210> SEQ ID NO 99
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cctgtgatgg gcatcgcacc cgagtctaaa g                                      31

<210> SEQ ID NO 100
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ctttagactc gggtgcgatg cccatcacag g                                      31

<210> SEQ ID NO 101
<211> LENGTH: 40
<212> TYPE: PRT
<213> ORGANISM: Zea mays

<400> SEQUENCE: 101

Met Gly Ile Ala Thr Glu Ser Lys Ala Thr Thr Glu Ser Val Tyr Ser
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 102
<211> LENGTH: 40
<212> TYPE: PRT
<213> ORGANISM: Zea mays

<400> SEQUENCE: 102

Met Gly Ile Ala Thr Glu Ser Lys Ala Thr Thr Glu Ser Val Tyr Ser
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 103
<211> LENGTH: 40
<212> TYPE: PRT
<213> ORGANISM: Zea mays

<400> SEQUENCE: 103

Met Gly Ile Ala Ser Glu Ser Lys Ala Thr Thr Glu Ser Val Tyr Ser
```

```
1               5                  10                 15
Ala Ala Leu Ala Leu Gly Ile Ala Asn Gln Leu Thr Asn Ile Leu Arg
            20                 25                 30

Asp Val Gly Glu Asp Ala Arg Arg
            35                 40
```

<210> SEQ ID NO 104
<211> LENGTH: 40
<212> TYPE: PRT
<213> ORGANISM: Zea mays

<400> SEQUENCE: 104

```
Met Gly Ile Ala Pro Glu Ser Lys Ala Thr Thr Glu Ser Val Tyr Ser
1               5                  10                 15

Ala Ala Leu Ala Leu Gly Ile Ala Asn Gln Leu Thr Asn Ile Leu Arg
            20                 25                 30

Asp Val Gly Glu Asp Ala Arg Arg
            35                 40
```

<210> SEQ ID NO 105
<211> LENGTH: 40
<212> TYPE: PRT
<213> ORGANISM: Zea mays

<400> SEQUENCE: 105

```
Met Gly Ile Ala Thr Glu Ser Lys Ala Thr Thr Glu Ser Val Tyr Ser
1               5                  10                 15

Ala Ala Leu Ala Leu Gly Ile Ala Asn Gln Leu Thr Asn Ile Leu Arg
            20                 25                 30

Asp Val Gly Glu Asp Ala Arg Arg
            35                 40
```

<210> SEQ ID NO 106
<211> LENGTH: 40
<212> TYPE: PRT
<213> ORGANISM: Zea mays

<400> SEQUENCE: 106

```
Met Gly Ile Ala Thr Glu Ser Lys Ala Thr Thr Glu Ser Val Tyr Ser
1               5                  10                 15

Ala Ala Leu Ala Leu Gly Ile Ala Asn Gln Leu Thr Asn Ile Leu Arg
            20                 25                 30

Asp Val Gly Glu Asp Ala Arg Arg
            35                 40
```

<210> SEQ ID NO 107
<211> LENGTH: 40
<212> TYPE: PRT
<213> ORGANISM: Zea diploperennis

<400> SEQUENCE: 107

```
Met Gly Ile Ala Pro Glu Ser Lys Ala Thr Thr Glu Ser Val Tyr Ser
1               5                  10                 15

Ala Ala Leu Ala Leu Gly Ile Ala Asn Gln Leu Thr Asn Ile Leu Arg
            20                 25                 30

Asp Val Gly Glu Asp Ala Arg Arg
            35                 40
```

<210> SEQ ID NO 108
<211> LENGTH: 40

<212> TYPE: PRT
<213> ORGANISM: Zea luxurians

<400> SEQUENCE: 108

Met Gly Ile Ala Pro Glu Ser Lys Ala Thr Thr Glu Ser Val Tyr Ser
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 109
<211> LENGTH: 40
<212> TYPE: PRT
<213> ORGANISM: Zea mays

<400> SEQUENCE: 109

Met Gly Ile Ala Pro Glu Ser Lys Ala Thr Thr Glu Ser Val Tyr Ser
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 110
<211> LENGTH: 40
<212> TYPE: PRT
<213> ORGANISM: Aegilops tauschii

<400> SEQUENCE: 110

Met Gly Ile Ala Pro Glu Ser Lys Ala Thr Ala Glu Ser Val Tyr Gly
1               5                   10                  15

Ala Ala Leu Ala Leu Gly Leu Ala Asn Gln Leu Thr Asn Ile Leu Arg
            20                  25                  30

Asp Val Gly Glu Asp Ala Arg Arg
        35                  40

<210> SEQ ID NO 111
<211> LENGTH: 40
<212> TYPE: PRT
<213> ORGANISM: Coix lacryma-jobi

<400> SEQUENCE: 111

Met Gly Ile Ala Pro Glu Ser Lys Ala Thr Thr Glu Ser Val Tyr Ser
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 112
<211> LENGTH: 40
<212> TYPE: PRT
<213> ORGANISM: Narcissus pseudonarcissus

<400> SEQUENCE: 112

Met Gly Ile Ala Pro Glu Ser Leu Ala Glu Ala Glu Ser Val Tyr Asn
1               5                   10                  15

Ala Ala Leu Ala Leu Gly Ile Ala Asn Gln Leu Thr Asn Ile Leu Arg
            20                  25                  30

-continued

Asp Val Gly Glu Asp Ala Arg Arg
        35                  40

<210> SEQ ID NO 113
<211> LENGTH: 40
<212> TYPE: PRT
<213> ORGANISM: Narcissus tazetta

<400> SEQUENCE: 113

Met Gly Ile Ala Pro Glu Ser Leu Ala Glu Ala Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 114
<211> LENGTH: 40
<212> TYPE: PRT
<213> ORGANISM: Sorghum bicolor

<400> SEQUENCE: 114

Met Gly Ile Ala Pro Glu Ser Lys Ala Thr Thr Glu Ser Val Tyr Ser
1               5                   10                  15

Ala Ala Leu Ala Leu Gly Ile Ala Asn Gln Leu Thr Asn Ile Leu Arg
            20                  25                  30

Asp Val Gly Glu Asp Ala Thr Arg
        35                  40

<210> SEQ ID NO 115
<211> LENGTH: 40
<212> TYPE: PRT
<213> ORGANISM: Sorghum bicolor

<400> SEQUENCE: 115

Met Gly Ile Ala Pro Asp Ser Lys Ala Ser Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 116
<211> LENGTH: 40
<212> TYPE: PRT
<213> ORGANISM: Sorghum bicolor

<400> SEQUENCE: 116

Met Gly Ile Ser Pro Asp Ser Arg Ala Ala Thr Glu Thr Val Tyr Lys
1               5                   10                  15

Gly Ala Leu Ala Leu Gly Leu Ala Asn Gln Leu Thr Asn Ile Leu Arg
            20                  25                  30

Asp Val Gly Glu Asp Ala Arg Arg
        35                  40

<210> SEQ ID NO 117
<211> LENGTH: 40
<212> TYPE: PRT
<213> ORGANISM: Tripsacum sp.

<400> SEQUENCE: 117

```
Met Gly Ile Ala Pro Glu Ser Lys Ala Thr Thr Glu Ser Val Tyr Ser
1               5                  10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 118
<211> LENGTH: 40
<212> TYPE: PRT
<213> ORGANISM: Triticum aestivum

<400> SEQUENCE: 118

Met Gly Ile Ala Pro Asp Ser Lys Ala Thr Ala Glu Ser Val Tyr Gly
1               5                  10                  15

Ala Ala Leu Ala Leu Gly Leu Ala Asn Gln Leu Thr Asn Ile Leu Arg
            20                  25                  30

Asp Val Gly Glu Asp Ala Arg Arg
        35                  40

<210> SEQ ID NO 119
<211> LENGTH: 40
<212> TYPE: PRT
<213> ORGANISM: Thinopyrum ponticum

<400> SEQUENCE: 119

Met Gly Ile Ala Pro Glu Ser Lys Ala Thr Ala Glu Ser Val Tyr Gly
1               5                  10                  15

Thr Ala Leu Ala Leu Gly Leu Ala Asn Gln Leu Thr Asn Ile Leu Arg
            20                  25                  30

Asp Val Gly Glu Asp Ala Arg Arg
        35                  40

<210> SEQ ID NO 120
<211> LENGTH: 40
<212> TYPE: PRT
<213> ORGANISM: Actinidia deliciosa

<400> SEQUENCE: 120

Met Gly Ile Ala Pro Asp Ser Leu Ala Thr Thr Glu Ser Val Tyr Asn
1               5                  10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 121
<211> LENGTH: 40
<212> TYPE: PRT
<213> ORGANISM: Brassica rapa

<400> SEQUENCE: 121

Met Gly Ile Asp Pro Lys Ser Lys Ala Thr Thr Glu Ser Val Tyr Asn
1               5                  10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 122
```

```
<211> LENGTH: 40
<212> TYPE: PRT
<213> ORGANISM: Carica papaya

<400> SEQUENCE: 122

Met Gly Ile Ala Pro Glu Ser Gln Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 123
<211> LENGTH: 40
<212> TYPE: PRT
<213> ORGANISM: Coffea canephora

<400> SEQUENCE: 123

Met Gly Ile Ala Pro Glu Ser Lys Ala Thr Val Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Thr Arg
        35                  40

<210> SEQ ID NO 124
<211> LENGTH: 40
<212> TYPE: PRT
<213> ORGANISM: Citrus maxima

<400> SEQUENCE: 124

Met Gly Ile Ala Pro Asp Ser Gln Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Gly Val Gly Glu Asp Ala Gln Arg
        35                  40

<210> SEQ ID NO 125
<211> LENGTH: 40
<212> TYPE: PRT
<213> ORGANISM: Citrus unshiu

<400> SEQUENCE: 125

Met Gly Ile Ala Pro Asp Ser Gln Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 126
<211> LENGTH: 40
<212> TYPE: PRT
<213> ORGANISM: Citrofortunella mitis

<400> SEQUENCE: 126

Met Gly Ile Ala Pro Asp Ser Gln Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30
```

-continued

Asp Val Gly Glu Asp Ala Gln Arg
        35                  40

<210> SEQ ID NO 127
<211> LENGTH: 40
<212> TYPE: PRT
<213> ORGANISM: Cucumis melo

<400> SEQUENCE: 127

Met Gly Ile Ala Pro Glu Ser Gln Ala Ser Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 128
<211> LENGTH: 40
<212> TYPE: PRT
<213> ORGANISM: Daucus carota

<400> SEQUENCE: 128

Met Gly Ile Ala Pro Asn Ser Gln Ala Thr Thr Glu Ser Val Tyr Asn
1               5                   10                  15

Ala Ala Leu Ala Leu Gly Leu Ala Asn Gln Leu Thr Asn Ile Leu Arg
            20                  25                  30

Asp Val Gly Glu Asp Ala Arg Arg
        35                  40

<210> SEQ ID NO 129
<211> LENGTH: 40
<212> TYPE: PRT
<213> ORGANISM: Diospyros kaki

<400> SEQUENCE: 129

Met Gly Ile Ala Pro Glu Ser Gln Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 130
<211> LENGTH: 40
<212> TYPE: PRT
<213> ORGANISM: Elaeagnus umbellate

<400> SEQUENCE: 130

Met Gly Ile Ala Pro Glu Ser Gln Ala Thr Thr Glu Ser Ile Tyr Asn
1               5                   10                  15

Ala Ala Leu Ala Leu Gly Ile Ser Asn Gln Leu Thr Asn Ile Leu Arg
            20                  25                  30

Asp Val Gly Glu Asp Ala Arg Arg
        35                  40

<210> SEQ ID NO 131
<211> LENGTH: 40
<212> TYPE: PRT
<213> ORGANISM: Ipomoea sp.

<400> SEQUENCE: 131

Met Gly Ile Ala Pro Glu Ser Lys Ala Thr Thr Glu Ser Val Tyr Asn
1               5                   10                  15

Ala Ala Leu Ala Leu Gly Ile Ala Asn Gln Leu Thr Asn Ile Leu Arg
                20                  25                  30

Asp Val Gly Glu Asp Ala Arg Arg
            35                  40

<210> SEQ ID NO 132
<211> LENGTH: 40
<212> TYPE: PRT
<213> ORGANISM: Manihot esculenta

<400> SEQUENCE: 132

Met Gly Ile Ala Pro Glu Ser Gln Ala Ser Thr Glu Ser Val Tyr Asn
1               5                   10                  15

Ala Ala Leu Ala Leu Gly Ile Ala Asn Gln Leu Thr Asn Ile Leu Arg
                20                  25                  30

Asp Val Gly Glu Asp Ala Arg Arg
            35                  40

<210> SEQ ID NO 133
<211> LENGTH: 40
<212> TYPE: PRT
<213> ORGANISM: Manihot esculenta

<400> SEQUENCE: 133

Met Gly Ile Ala Pro Glu Ser Gln Ala Ser Thr Glu Ser Val Tyr Asn
1               5                   10                  15

Ala Ala Leu Ala Leu Gly Ile Ala Asn Gln Leu Thr Asn Ile Leu Arg
                20                  25                  30

Asp Val Gly Glu Asp Ala Arg Arg
            35                  40

<210> SEQ ID NO 134
<211> LENGTH: 40
<212> TYPE: PRT
<213> ORGANISM: Momordica charantia

<400> SEQUENCE: 134

Met Gly Ile Ala Pro Asp Ser Glu Ala Ser Thr Glu Ser Val Tyr Asn
1               5                   10                  15

Ala Ala Leu Ala Leu Gly Ile Ala Asn Gln Leu Thr Asn Ile Leu Arg
                20                  25                  30

Asp Val Gly Glu Asp Ala Arg Arg
            35                  40

<210> SEQ ID NO 135
<211> LENGTH: 40
<212> TYPE: PRT
<213> ORGANISM: Nicotiana tabacum

<400> SEQUENCE: 135

Met Gly Ile Ala Pro Glu Ser Lys Ala Thr Thr Glu Ser Val Tyr Asn
1               5                   10                  15

Ala Ala Leu Ala Leu Gly Leu Ala Asn Gln Leu Thr Asn Ile Leu Arg
                20                  25                  30

Asp Val Gly Glu Asp Ala Arg Arg
            35                  40

-continued

```
<210> SEQ ID NO 136
<211> LENGTH: 40
<212> TYPE: PRT
<213> ORGANISM: Oncidium sp.

<400> SEQUENCE: 136

Met Gly Ile Ala Pro Glu Ser Asp Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Thr Arg
        35                  40

<210> SEQ ID NO 137
<211> LENGTH: 40
<212> TYPE: PRT
<213> ORGANISM: Populus trichocarpa

<400> SEQUENCE: 137

Met Gly Ile Ala Pro Glu Ser Gln Ala Ser Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 138
<211> LENGTH: 40
<212> TYPE: PRT
<213> ORGANISM: Prunus mume

<400> SEQUENCE: 138

Met Gly Ile Ser Pro Glu Ser Gln Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 139
<211> LENGTH: 40
<212> TYPE: PRT
<213> ORGANISM: Ricinus communis

<400> SEQUENCE: 139

Met Gly Ile Ala Pro Glu Ser Gln Ala Ala Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 140
<211> LENGTH: 40
<212> TYPE: PRT
<213> ORGANISM: Salicornia europaea

<400> SEQUENCE: 140

Met Gly Ile Ala Pro Glu Ser Lys Ala Pro Thr Glu Ser Val Tyr Asn
1               5                   10                  15

Ala Ala Leu Ala Leu Gly Ile Ala Asn Gln Leu Thr Asn Ile Leu Arg
```

Asp Val Gly Glu Asp Ser Arg Arg
        35                  40

<210> SEQ ID NO 141
<211> LENGTH: 40
<212> TYPE: PRT
<213> ORGANISM: Solanum lycopersicum

<400> SEQUENCE: 141

Met Gly Ile Ala Pro Glu Ser Lys Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 142
<211> LENGTH: 40
<212> TYPE: PRT
<213> ORGANISM: Solanum lycopersicum

<400> SEQUENCE: 142

Met Gly Ile Ala Pro Glu Ser Lys Ala Thr Thr Glu Ser Val Tyr Asn
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 143
<211> LENGTH: 40
<212> TYPE: PRT
<213> ORGANISM: Vitis vinifera

<400> SEQUENCE: 143

Met Gly Ile Ala Pro Glu Ser Gln Ala Thr Thr Glu Ser Val Tyr Lys
1               5                   10                  15

Ala Ala Leu Ala Leu Gly Ile Ala Asn Gln Leu Thr Asn Ile Leu Arg
            20                  25                  30

Asp Val Gly Glu Asp Ala Arg Arg
        35                  40

<210> SEQ ID NO 144
<211> LENGTH: 5
<212> TYPE: PRT
<213> ORGANISM: Unknown
<220> FEATURE:
<223> OTHER INFORMATION: Description of Unknown: PSY1 motif
      sequence

<400> SEQUENCE: 144

Asp Glu Leu Val Asp
1               5

```
<210> SEQ ID NO 145
<211> LENGTH: 5
<212> TYPE: PRT
<213> ORGANISM: Unknown
<220> FEATURE:
<223> OTHER INFORMATION: Description of Unknown: PSY1 motif
      sequence

<400> SEQUENCE: 145

Asp Val Gly Glu Asp
1               5
```

METHOD FOR MODIFYING CAROTENOID BIOSYNTHESIS IN PLANTS

CROSS-REFERENCE TO RELATED APPLICATIONS

This application is a U.S. National Phase Application of, and claims priority to, International Patent Application Number PCT/US2013/055069 filed 15 Aug. 2013, which claims the benefit of U.S. Provisional Application No. 61/683,494, filed 15 Aug. 2012, each of which is incorporated by reference in their entities.

BACKGROUND OF THE INVENTION

Carotenoids are a large class of yellow, orange and red lipophilic structures synthesized by all photosynthetic organisms. In plants, carotenoids play multiple roles such as photosynthetic light harvesting, protection against light and heat stress, and as precursors to hormones that mediate stress and developmental signalling. Carotenoid antioxidants increase heat and light stress tolerance by protecting membranes from reactive oxygen species (ROS) and lipid peroxidation. Concentrated in fibrillar plastoglobuli of fruit chromoplasts, carotenoids are attractants to animals that serve as plant seed distributors. Certain carotenoids in the endosperm tissue provide nutritional value and have been targets for improvement, especially in cereal crops of the grass family.

The biosynthetic pathway of carotenoids occurs in plastids where the lipophilic carotenoids accumulate in envelope/thylakoid membranes and plastoglobuli. Carotenoids are synthesized in both light and dark-grown tissues, such as leaves, endosperm, and roots. In the dark, leaf tissues develop etioplasts with rudimentary prolamellar bodies, which are the precursors for thylakoids and support low levels of carotenoid biosynthesis. In the light, leaves turn green due to development of highly specialized chloroplasts filled with complex photosynthetic systems. Carotenoids are distributed differently in etioplasts and chloroplasts that might require differential localization of their biosynthetic enzymes as well.

Phytoene synthase (PSY) catalyzes the committed step to carotenoid biosynthesis and is a key target for pathway engineering. There are up to three PSY isozymes in evolutionarily distant plants, including all the major food staples in the grasses and other crops of agronomic importance. Different PSY isozymes mediate carotenogenesis in particular tissues, in response to developmental and physiological signals. Allele-specific variation accounts for yellow endosperm maize and yellow rooted cassava.

The core carotenoid biosynthetic pathway consists of about 10 enzymes. However, the location of the biosynthetic pathway as a complete entity for controlling the unique spatial distribution of carotenoids is unknown. Moreover, this pathway must respond to environmental and developmental signals to link photomorphogenesis, photoprotection, and stress responses with location-specific carotenoid synthesis and degradation. It has long been desired to understand the nature of this dynamic pathway landscape and how isozymes and allelic variants fit into the picture.

According to recent proteomic studies on Arabidopsis chloroplasts, many of the carotenoid biosynthetic pathway enzymes are exclusively localized to envelope membranes. Only a few carotenoid enzymes are found in thylakoids: xanthophyll cycle enzymes and phytoene desaturase (PDS). For example, in pepper fruit chromoplasts, most carotenoid enzymes are localized to plastoglobuli. In maize proteomic studies, the only carotenoid enzymes detected were PDS and □-carotene desaturase (ZDS) that were respectively found in membrane fractions of bundle sheath and mesophyll cells. Carotenoids are found in both cell types, yet other carotenoid biosynthetic enzymes were undetectable. Chloroplast suborganellar localization of the key pathway enzyme, PSY, has yet to be detected by proteomic analysis.

As a result of this invention, it has been discovered that PSY isozymes differ in chloroplast suborganellar localization and that overexpression of naturally occurring allelic variants produces striking differences in localization and profound effects on chloroplast architecture.

BRIEF DESCRIPTION OF THE FIGURES

FIG. 1. Transient expression of various PSY-GFP fusion constructs in leaf mesophyll protoplasts.

A. Expression in etiolated maize protoplasts. All PSYs from maize and rice, except $_{zm}$PSY1, are localized to specific speckles. $_{zm}$PSY1 is localized to stroma and associated to prolamellar bodies. Chl: chlorophyll autofluorescence, concentrated in a partial area of an etioplast.

B. Expression of $_{zm}$PSYs and $_{os}$PSYs in green maize protoplasts and of $_{at}$PSY-RFP in green bean protoplasts. All PSY from maize, rice and Arabidopsis, except $_{zm}$PSY1, are localized to specific speckles. $_{zm}$PSY1 is localized to stroma. Chl: chlorophyll autofluorescence, occupying the entire area of a chloroplast. Bar=10 μm.

FIG. 2. Plastoglobuli localization of various proteins in mesophyll protoplasts.

A. Transient expression of $_{zm}$PG2-RFP, suggesting localization to plastoglobuli.
1. Expression in bean cotyledon protoplasts.
2. Expression in green maize protoplasts.
3. Expression in etiolated maize protoplasts.
**1 and 2 show plastoglobular localization, 3 shows stromal localization.

B. Transient co-expression of $_{zm}$PSY2-GFP (1) and $_{zm}$PSY3-GFP (2) with $_{zm}$PG2-RFP. $_{zm}$PSYs and $_{zm}$PG2 are co-localized, as seen on merged image, indicating plastoglobular localization of $_{zm}$PSY2 and $_{zm}$PSY3. Chl: chlorophyll autofluorescence. Bar=10 μm.

FIG. 3. Import of proteins into chloroplasts. Protein precursors were made by in vitro transcription/translation. Protein precursors were incubated with isolated chloroplasts for import and processing to the mature forms. Mature proteins were resistant to thermolysin treatment of chloroplasts post-import and of smaller mass compared to the unimported precursors.

A. import of proteins with known localization used as a control for fraction purity: 16/EGFP (a transit peptide of spinach OE16 of oxygen evolution system from thylakoid lumen, fused with EGFP), LHCP (light-harvesting chlorophyll a/b binding pea protein localized in thylakoid membranes), and Toc34 (a component of the protein transport complex from the outer envelope membrane).

B. import of maize PSYs. Arrow—mature processed protein. Star—20 kDa band.
kDa—molecular weight marker
P—precursor (1 μl of the translation mix)
I—import of radiolabelled precursor protein into intact chloroplasts
T—thermolysin treated chloroplasts
M—membrane fraction
MA—purified membrane fraction (after alkaline treatment)
S—soluble fraction FIG. 4. Alignment of PSY aminoacids for all enzymes used in experiments adjusted to secondary SQS structure. #168: aminoacid represented by asparagine (N) in $_{zm}$PSY1 and serine (S) in all other PSYs. #257: aminoacid represented by threonine (T) in $_{zm}$PSY1 and proline (P) in all other PSYs. #174, 190: respective aminoacids were shown to affect the activity of PSY in cassava and tomato. #285: mutation at this site inactivates SQS (Gu et al, 1998). S-putative cleavage site for chloroplast transit sequence, predicted by ChloroP. XXXXX—psy and sqs signature motif 1 and 2 (conserved pattern). XXXXX—a-helix, predicted by Metaserver based on SQS structure. Box—DXXXD putative active site, mutagenesis of $D_{285}$ inactivates the enzyme. (*)—62 aa of C-terminus of SQS sequence were truncated. FIG. 4 discloses SEQ ID NOS 1-7, respectively, in order of appearance.

FIG. 5. Alignment of phytoene synthase amino acid sequences. BLAST alignment of $_{zm}$PSY1 to all PSY sequences available from NCBI. Box—DXXXD putative active site, based on SQS alignment. Highlight—amino acids 168 and 257. Amino acid numbers refer to $_{zm}$PSY1 sequence. FIG. 5 discloses SEQ ID NOS 8-50 and 101-143, respectively, in order of appearance (top to bottom, left to right)

FIG. 6. Transient expression of $_{zm}$PSY1-NP-GFP and its mutagenized variants in etiolated maize protoplasts. $_{zm}$PSY1-NP is forming characteristic spikes in 30% of cases (see central protoplast), the rest 70% it is soluble (top left corner). $_{zm}$PSY1-SP, $_{zm}$PSY1-NS and $_{zm}$PSY1-ST are localized evenly inside plastids, suggesting soluble stromal localization. Chl: chlorophyll autofluorescence. Bar=10 μm.

FIG. 7. Sequence of $_{zm}$PSY1s with transit peptide removed threaded onto crystal structure of squalene synthase.

A. Graphical representation of RMSD data on $_{zm}$PSY1 modeling. Blue: $_{zm}$PSY1, green: $_{zm}$PSY1-NP. Star: amino acid #257. Red arrow: perturbed region. Black double arrow: regions $_{159}DELVD_{163}$ (SEQ ID NO: 144) and $_{285}DVGED_{289}$ (SEQ ID NO: 145) as putative active site.

B. RMSD data showing mean distance (y-axis, in angstroms) between atoms of the three superimposed $_{zm}$PSY structures (numbered $_{zm}$PSY amino acids shown on x-axis). Red: $_{zm}$PSY1-NP, green: $_{zm}$PSY1-SP, blue: marker to show location in sequence of amino acids 168, 174, 190 and 257.

FIG. 8. Overexpression of proteins with known location in etiolated maize protoplasts.

A. soluble GFP (protoplasts transformed with pUC35S-sGFP-Nos), GFP is localized to cell cytoplasm.

B. LHCP-GFP (protoplasts transformed with pUC35S-LHCP-sGFP-Nos), LHCP is an integral protein from thylakoid membrane and colocalized with chlorophyll fluorescence.

C. AtAPG1 (protoplasts transformed with pFB70),

D. AtTic40 (protoplasts transformed with pFB71). AtAPG1 and AtTic40 are proteins from chloroplast inner envelope membrane and demonstrate half-moon or circle pattern correspondingly.

Chl—chlorophyll autofluorescence. Bar=10 μm.

FIG. 9. Hidden 3D ("third eye") stereogram of transiently expressed $_{zm}$PSY1-NP-GFP in etiolated maize protoplasts. $_{zm}$PSY1-NP-GFP is forming characteristic spikes. Stereogram prepared from original microscopic image by Hidden 3D studio, USA. It can be viewed by unfocusing the eyes and looking "through" the image.

FIG. 10. Transient expression of $_{zm}$PSY-GFP variants in etiolated maize protoplasts from PSY1 knockout line.

FIG. 11. Spectral dye separation for transiently expressed GFP-fusion proteins in maize PSY1 knockout leaf protoplasts. Different fusion protein constructs were transiently expressed in protoplasts, isolated from etiolated leaves of maize PSY1 knockout plants. GFP and carotenoid fluorescent spectra were separated using Spectral Dye Separation tool in LAS AF software (Leica Microsystems). Carotenoids have a low fluorescence emission between 500 and 650 nm which can be excited by a 488 nm laser. The software separates the carotenoid emission from the GFP emission. To eliminate any background carotenoid fluorescence in the absence of a PSY transgene, we used protoplasts prepared form $_{zm}$PSY1-knockout maize y1-8549 which are unable to produce carotenoids in the absence of the transgenically supplied PSY.

A. Soluble GFP without any protein or transit peptide attached, localized to protoplast cytoplasm Soluble cytoplasmic GFP, used as a negative control and GFP spectrum reference, showed no carotenoid emission B. $_{zm}$PSY1-NP-GFP—Fibrils formed by $_{zm}$PSY1-NP have bright fluorescence in the carotenoid channel suggesting presence of concentrated carotenoids.

C. $_{zm}$PSY1-NP-E-GFP—Such fluorescence disappeared, showing no fibrils when non-active $_{zm}$PSY1-NP-E was overexpressed in etioplasts.

D. $_{zm}$PSY1-NT-GFP—A low level of carotenoid fluorescence was observed in etioplasts carrying overexpressed $_{zm}$PSY1-NT which might be due to a basal level of carotenoid biosynthesis in leaves due to inactivity of $_{zm}$PSY when not attached to membranes.

E. $_{zm}$PSY2-GFP—punctuated dots, formed in etioplasts by $_{zm}$PSY2-GFP show bright fluorescence in the carotenoid channel suggesting presence of concentrated carotenoids F. $_{zm}$PSY3-GFP—Punctuated dots, formed in etioplasts by $_{zm}$PSY3-GFP show bright fluorescence in the carotenoid channel suggesting presence of concentrated carotenoids.

G. LHCP-GFP (negative control of plastid protein fused with GFP; LHCP is a not involved in carotenoid biosynthesis). In contrast, only background level of fluorescence is observed when a control chloroplast-localized noncarotenoid protein is introduced (integral thylakoid membrane protein LHCP.

GFP, Carotenoids—maximum projection of corresponding isolated fluorescent spectra;

Bright field—bright field image of the protoplast. Bar=10 μm.

FIG. 12. E. coli complementation test. E. coli Top 10 with pACCAR25☐crtB carrying carotenoid biosynthetic enzymes for zeaxanthin production, but lacking the PSY enzyme, was transformed with different mutagenized variants of $_{zm}$PSY1. Active PSY enzymes were able to complement the pathway which resulted in zeaxanthin production. Zeaxanthin was extracted from pelleted cells by methanol and then analyzed by HPLC to detect the relative amount produced, which was calculated as peak area divided by OD of the E. coli culture. $_{zm}$PSY1, $_{zm}$PSY1-NP were active in this test, $_{zm}$PSY1-$D_{285}$E was inactive. An empty expression vector was used as a negative control.

SUMMARY OF THE INVENTION

The present invention related to a method for providing increased carotenoid content to a plant and for improving stress resistance to climate changes in a plant comprising. The method involves overexpressing naturally occurring allelic variants of phytoene synthase (PSY) in the plant.

In one embodiment, the allelic variant is the NP variant of phytoene synthase 1 (PSY1).

In another aspect, the invention provides a method for selecting plants with increased carotenoid content and/or having improved stress resistance to climate changes. The method involves selecting plants in which naturally occurring allelic variants of phytoene synthase (PSY) are overexpressed in said plant.

In another embodiment, the allelic variant is the NP variant of phytoene synthase 1 (PSY1).

DETAILED DESCRIPTION OF THE INVENTION

As a rate-controlling enzyme of the pathway, PSY has been used extensively for metabolic engineering of the carotenoid biosynthetic pathway in plants despite limited understanding of its plastid suborganellar location. Confocal microscopy of fluorescently tagged PSYs provided a glimpse into the carotenoid biosynthetic microenvironment in leaf mesophyll cells.

PSYs are highly conserved in their amino acid sequence (See FIG. 4). Yet, small variations in a region that must be important for activity have been discovered. This region lies adjacent to a common signature motif found in isoprenoid synthases. These natural variants include variations in amino acid residues at positions 168 and 257 of PSY. See Example 3 and Table 1 below.

As will be discussed below, $_{zm}$PSY1 of B73 has the allele in yellow endosperm $N_{168}T_{257}$ or "NT." If $T_{257}$ is changed to proline, an "NP" variation is produced. If $T_{257}$ is changed to a serine an "NS" variation is produced.

It has been discovered that the effect of the NP variation on fibril formation occurred in etioplasts from a subpopulation of protoplasts found among the complex population of cell-types shown to exist in leaves. Whole-tissue carotenoid or proteomic extraction would otherwise have masked these perturbations on enzyme location and carotenoid accumulation taking place in subpopulations of cells.

The present invention elucidates the physical location of a key pathway enzyme that must interface with a complex and dynamic metabolon in the context of the suborganellar architecture that is unique to plastid type in specific tissues. More importantly, it has been discovered that not all PSYs localize identically. This discovery serves as a source of caution and also opportunity for improving carotenoid targets needed, for example, to improve seed nutritional quality or plant stress resistance to address challenges of food security and biofuels in the face of global climate change.

It has been discovered that PSY isozymes target to unique chloroplast suborganellar sites and small sequence variation and enzyme activity of PSY1 alters enzyme localization. This is the first time that PSYs have been localized to plastoglobules. Plastoglobuli are found in all plastids although their specific function is not well understood. Plastoglobuli range in size from 60-4000 nm and their composition varies depending on plastid type and plant source. In chloroplasts, plastoglobuli associate with thylakoids, while details of plastoglobular association in non-photosynthetic plastids are sparse.

In general, plastoglobuli contain carotenoids, plastoquinones, tocopherols, and various proteins surrounded by a distinctively-composed lipid monolayer that is contiguous with the outer layer of the thylakoid lipid bilayer. Fibrilins, the major proteins of plastoglobuli, maintain the structure of the globules and assist in the globular-fibril transition to store high amounts of carotenoids synthesized during chromoplast development. Plastoglobuli also enlarge and proliferate in response to abiotic stress (e.g. high light, drought, salt, heat and nitrogen starvation). These stress conditions induce accumulation of carotenoids and/or their apocarotenoid products, and the expression of core plastoglobuli protein genes correlates with the expression of several enzymes from the carotenoid pathway. The importance of plastoglobuli in modulating plant metabolism is beginning to gain attention. Overexpression of the tocopherol cyclase VTE1, a plastoglobular enzyme, resulted in proliferation of plastoglobuli and an increased level of tocopherols.

As a result of the herein invention, it has been discovered that activity of the overexpressed PSY1, with the naturally-occurring NP sequence variation, may exert an effect on fibrillar plastoglobule architecture, since the active enzyme caused plastoglobular fibril formation, which disappeared when the PSY active site was mutated. In both VTE1 and PSY1 cases, overexpression of plastoglobular-associated enzymes caused physical changes in the site of carotenoid sequestration. Taken together, increased levels of rate-controlling plastoglobule-located vitamin E and carotenoid biosynthesis enzymes might drive plastid structural changes needed to provide a sink for the hydrophobic biosynthetic pathway products.

Establishment of PSY localization leads to the question of how and where the entire pathway is reconstituted. Carotenoids are found on envelope and thylakoid membranes, implying that either the pathway forms on two membrane sites or that carotenoids are transported by an unknown mechanism. Carotenoid metabolons (enzyme complexes) are predicted to exist on the basis of high molecular weight complexes containing PSY or other carotenoid enzymes. A recent study showed that the capacity for enzymes to interact was associated with enhanced carotenoid pathway activity. Metabolon-associated enzymes could facilitate substrate channeling, as has been suggested by the absence of carotenoid pathway intermediates, except in cases where the pathway is artificially blocked.

It is significant that PSY1 with NT or SP combinations behaved similarly in localization, in contrast to NP which was shown to have a dramatic effect on plastid architecture. The present invention indicates that use of the NP variation may be more effective in enhancing production of carotenoids in certain tissues. For example, PSY1 is naturally expressed in etiolated tissue and known to provide thermal tolerance which is lost in plants that are unable to make PSY1. Indeed, if the NP variant is more effective in promoting carotenoids in etioplasts, this allelic variant could be valuable in selecting plants that are more resilient to climate change.

As a result of the herein invention, it has been discovered that *Arabidopsis* PSY is localized to plastoglobules. Based on proteomics studies of *Arabidopsis* chloroplasts, PDS is on the envelope and thylakoid and ZDS is in the stroma. Together with PSY, it is possible to form a complex to produce prolycopene, a pathway intermediate. The absence of detectable prolycopene suggests that additional enzymes are recruited, but these are not detected by proteomics which may be due to limitations of the proteomics methodologies. In contrast to the enzyme localization seen in *Arabidopsis* chloroplasts, in chromoplasts, which exhibit an exaggerated developmental induction of carotenoid accumulation, the proteomics analysis revealed that most of the enzymes were found in plastoglobules. Therefore, the possibility exists that the complexes are forming in a dynamic fashion and "recruited as needed."

The present invention provides methods for increasing nutritional value in a plant or enhancing stress resistance to climate change in a plant by metabolic engineering of carotenoids in plants. There are known connections between induction of carotenoid enzymes and physical changes at the subcellular level. For example, morphological changes associated with carotenogenesis in development of chromoplasts include increases in fibrillins, plastoglobules, and biosynthetic enzymes. The different suborganellar localizations exhibited by allelic variants suggest that PSYs might be involved in mobilization of carotenoid pathway enzymes to mediate carotenogenesis at distinct locations, may control carotenogenesis by altered localization of PSY, and that localization of an active PSY may influence plastid ultrastructure. Clearly, not all PSYs behave identically, representing an opportunity for metabolic engineering or breeding with specific allelic variants.

Example 1: PSY Isozymes Exhibited Differential Locations in Maize Chloroplasts

To investigate localization of phytoene synthase isozymes, PSYs from two cereal crops, maize and rice, and a classical model plant *Arabidopsis* were chosen. Both maize and rice have three PSY isozymes and $_{zm}$PSY1, $_{zm}$PSY2, $_{zm}$PSY3 of *Z. mays* var. B73, and $_{os}$PSY1, $_{os}$PSY2 of *O. sativa* var. IR36 (Indica), and $_{os}$PSY3 of *O. sativa* var TP309 were tested. Maize variety B73 has yellow colored kernels due to carotenoid accumulation in the endosperm mediated by $_{zm}$PSY1 activity encoded by the maize yellow1 (y1) locus. Rice does not accumulate endosperm carotenoids. *Arabidopsis* has only one $_{at}$PSY.

The localization of PSYs was studied by transient expression of fluorescent protein fusions in plant leaf protoplasts. Protoplasts retain their tissue specificity after isolation, thereby reflecting in vivo conditions to observe localization of transiently expressed PSY proteins.

The above approach provides a great advantage for studying PSY, a low abundance protein that otherwise escapes detection in proteomic studies. Protoplast sources were chosen in consideration of different stages of plastid development. Protoplasts both from dark-grown tissues (etiolated protoplasts), or light-grown tissues (green protoplasts) were isolated. Also, monocot maize leaves as a protoplast source for expression of PSYs from monocotyledonous species maize and rice, and dicot beans for experiments on PSY from dicotyledonous *Arabidopsis* were chosen. Each PSY protein together with its chloroplast target peptide was C-terminally fused to synthetic green fluorescent (sGFP) or red fluorescent (RFP) protein, and transient expression was monitored by confocal microscopy.

To confirm reliability of the approach, proteins of known localization using protoplasts prepared from etiolated maize leaves were tested (FIG. 8). It was discovered that most, but not all, PSYs of all species studied were distributed in plastids the same way in both etiolated protoplasts (FIG. 1A), and green protoplasts (FIG. 1B), whether from monocots or dicots. These PSYs localized to chloroplasts in specific fixed speckles, distributed inside the plastid and attached to areas that displayed red chlorophyll fluorescence indicative of prolamellar bodies or thylakoids. The size and distribution of the speckles were suggestive of plastoglobuli: spherical lipid structures attached to thylakoid membranes of chloroplasts or distributed in chromoplast stroma. To define the nature of the speckles, transient expression with a protein from the fibrillin family was performed, since fibrillins are structural proteins of plastoglobuli. Maize plastoglobulin-2 ($_{zm}$PG2) was identified by BLAST search as a homolog to several fibrillins from *Arabidopsis* (AT4G04020, AT4G22240, AT2G35490, 80%-90% sequence similarity). $_{zm}$PG2 has a PAP-fibrillin domain, and is also homologous to the other *Arabidopsis* fibrillins of the superfamily (50-60% similarity). The isoelectric point (5.4) and hydrophobicity (GRAVY index, −0.142) of $_{zm}$PG2 were similar to *Arabidopsis* fibrillin FBN4, which is a core protein of plastoglobuli, although minor amounts of FBN4 are also identified by proteomic studies in chloroplast stroma. $_{zm}$PG2 was fused to RFP and expressed in bean and maize protoplasts (FIG. 2A). Indeed, in bean and maize green tissue protoplasts, the speckled pattern of $_{zm}$PG2-RFP was identical to the speckled pattern of the majority of PSYs. However, in etioplasts $_{zm}$PG2-RFP was distributed evenly throughout, suggesting a stromal localization for this fibrillin in dark-grown tissue. $_{zm}$PSY2-GFP and $_{zm}$PSY3-GFP along with $_{zm}$PG2-RFP in green protoplasts was also expressed (FIG. 2B). The GFP signal of the PSYs was distributed in speckles together with the RFP signal of $_{zm}$PG2. Merging of both signals confirmed co-localization of PSYs with $_{zm}$PG2; thus, the speckles are considered to be plastoglobuli.

$_{zm}$PSY1-GFP stood alone from the group of other PSYs. In etioplasts, $_{zm}$PSY1-GFP was distributed throughout, together with small bright (punctate) spots attached to membranes of red-fluorescent prolamellar bodies, very different in appearance from plastoglobuli in the case of all other PSYs. Homogeneous filling of plastids indicated a soluble, stromal location of $_{zm}$PSY1. In light-grown tissue, $_{zm}$PSY1-GFP was evenly distributed throughout the chloroplast. In chloroplasts, the association with membranes could not be seen, but should not be excluded due to limitations of image resolution.

Example 2: Import Experiments Confirmed Peripheral Membrane Binding of Chloroplast-Localized PSYs It has been discovered that by using transient expression, $_{zm}$PSY2 and $_{zm}$PSY3, as well as rice and *Arabidopsis* PSYs, localized to plastoglobuli structures, mostly attached to the surface of thylakoid membranes. Therefore, phytoene synthases were expected to associate with lipids/membranes. To confirm this, the three maize PSY isozymes were tested by chloroplast import assay. In vitro translated $^{35}$S labeled $_{zm}$PSY precursor proteins were imported into isolated pea chloroplasts, followed by chloroplast fractionation into three parts: soluble, membrane, and alkaline treated membrane (to purify from peripherally bound proteins) (FIG. 3).

After import, chloroplasts were treated with thermolysin to remove unimported proteins. The unimported protein, seen in the import samples of $_{zm}$PSY2 and $_{zm}$PSY3 as an upper band, completely disappeared after thermolysin treatment, and only the imported mature protein remained, being protected by the envelope membrane (FIG. 3B, arrow). Fractionation of these chloroplasts revealed that $_{zm}$PSY2 and $_{zm}$PSY3 were peripherally bound to chloroplast membranes. These results are consistent with association of these proteins with plastoglobuli, as was suggested by transient expression in protoplasts.

The results of chloroplast import of $_{zm}$PSY2 and $_{zm}$PSY3 were similar to $_{os}$PSYs. In import experiments with pea chloroplasts, $_{os}$PSYs are known to be associated with the membrane fraction (although alkaline treatment of the membrane fraction was not performed, the lack of integral membrane helices in the reported structural predictions of $_{os}$PSYs suggested that they were likely to be peripherally bound).

Compared to other PSYs, $_{zm}$PSY1 from yellow endosperm maize behaved uniquely in the import experiments, just as we found for $_{zm}$PSY1 localization in protoplasts. After thermolysin treatment, the envelope-associated precursor band disappeared as expected, leaving an undigested band of a mature protein ~42 kDa (FIG. 3B, arrow). However, a smaller band ~20 kDa appeared (FIG. 3B, star). This smaller peptide might be a part of $_{zm}$PSY1 that is located within the membrane and therefore is protected from protease treatment. The pattern after the thermolysin treatment looked similar to one of the integral proteins from the outer chloroplast membrane, Toc34. The inter-membrane and periplasm facing domains of Toc34 remained untouched by thermolysin. Fractionation of chloroplasts showed that $_{zm}$PSY1 is peripherally associated with membranes as found for the other PSYs.

Altogether, the results indicate that $_{zm}$PSY1 was somehow localized to chloroplasts in two forms. One form of $_{zm}$PSY1 is bound to the envelope membrane. A second form of $_{zm}$PSY1 is peripherally bound to thylakoids. The peripheral membrane association of $_{zm}$PSY1 agrees with the results of transient expression in etiolated protoplasts, where punctate spots of $_{zm}$PSY1-GFP were observed around prolamellar bodies.

Example 3: Single Amino Acid Variants Displayed Altered PSY1 Localization and Transformed Plastid Architecture Transient expression and import experiments suggested that almost all investigated PSYs were localized to plastoglobuli, regardless of whether the plants were grown in light or dark. $_{zm}$PSY1 was unique and exhibited dual localization to stroma and attached to membranes, as clearly seen in etioplasts (FIG. 1). Next, protein features responsible for differences in localization were identified. PSYs (FIG. 4), and searched for amino acids that are shared by all PSYs except for $_{zm}$PSY1 from yellow endosperm maize were aligned. A striking difference was found in the highly conserved coding region, at amino acid residue 257 which was a threonine ($T_{257}$) in $_{zm}$PSY1, as compared to proline (P) in other PSYs. Another position, 168, was occupied by asparagine in $_{zm}$PSY1 ($N_{168}$), in contrast with serine (S) in all other PSYs. BLAST alignment of $_{zm}$PSY1 from yellow endosperm maize line B73 used in the experiments, against other PSY sequences available from the NCBI database, showed that $T_{257}$ was characteristic for $_{zm}$PSY1 from 99% of the 79 maize varieties with yellow endosperm. In addition, $T_{257}$ was found in 30% of the 50 maize lines with white endosperm and two species of teosinte, the wild ancestor of maize which has the ancestral characteristic of white endosperm. 70% of white maize varieties had either $P_{257}$ or $S_{257}$; PSYs from all other plants carried proline at the corresponding position. $N_{168}$ was found in $_{zm}$PSY1 from all maize varieties, as well as in PSY of teosinte and some grass species; PSYs from other plants carried serine at the corresponding position (FIG. 5).

More detailed analysis of PSY1 sequences from maize and other grasses revealed that indeed, the only difference between $_{zm}$PSY1 amino acid sequences from yellow and white endosperm varieties and teosinte, was T/P/$S_{257}$. We also found some sequence differences within the chloroplast transit peptide around positions 52-55 (not shown). Since the transit peptide is processed after chloroplast import and does not affect enzyme activity, it was not included in this study.

To test if amino acids in positions 168 and 257 are important for localization, a set of variants was generated from $_{zm}$PSY1 of B73 (for which the allele in yellow endosperm is $N_{168}T_{257}$ or "NT"): with one amino acid change of $N_{168}$ to serine ($_{zm}$PSY1-ST) and an independent or additional change of $T_{257}$ to proline or serine ($_{zm}$PSY1-NP, $_{zm}$PSY1-NS, and $_{zm}$PSY1-SP). In addition, sites corresponding to 168 and 257, in $_{zm}$PSY2 and $_{os}$PSY1 (see Table 1 for explanation of all PSY variants) were mutated. PSY variant cDNAs were fused with GFP and expressed in maize protoplasts from both etiolated (FIG. 6) and green tissues (not shown). With the exception of $_{zm}$PSY1-NP, the stromal location of $_{zm}$PSY1 GFP-fusions was unchanged. Also, all $_{zm}$PSY2 and $_{os}$PSY1 variants retained localization phenotype to plastoglobuli (not shown) as seen for the progenitor maize PSY2 or rice PSY1 proteins.

The striking exception was seen in etiolated protoplasts, where $_{zm}$PSY1-NP, naturally found in some white varieties and teosinte, showed a surprising localization phenotype. In plastids of 30% of transformed protoplasts, $_{zm}$PSY1-NP-GFP formed unusual spikes, which stretched chloroplasts from inside causing a remarkable morphological change of plastid shape, from round elliptical to diamond with sharp corners where spikes touched the envelope membrane (FIG. 6 and FIG. 9). In the remaining 70% of protoplasts, $_{zm}$PSY1-NP-GFP was localized to stroma, similar to the phenotype exhibited by the progenitor yellow endosperm $_{zm}$PSY1. That is, a single residue change in the PSY1 protein altered PSY localization and plastid morphology. Remarkably, the double mutation of $_{zm}$PSY1-SP-GFP (where both 168 and 257 sites were mutated) restored stromal localization as exhibited by the progenitor $_{zm}$PSY1. The secondary mutation $N_{168}$ to $S_{168}$ appeared to counteract the effect of the single mutation $T_{257}$ to $P_{257}$. Interestingly, when $_{zm}$PSY1-NP-GFP was expressed in protoplasts from green seedlings, no fluorescent spikes or drastic morphological change in plastid shape was observed; the phenotype was the same as found with $_{zm}$PSY1 (FIG. 1B). The dramatic effect of the single residue change was only apparent in non-photosynthetic plastids.

To exclude the possible effect of the endogenous parent $_{zm}$PSY1 on localization pattern of overexpressed $_{zm}$PSY1, different PSY-GFP constructs in protoplasts of the y1-8549 maize line which lacks PSY1 were also expressed, and found no difference in localization of proteins to compare to ones in the B73 maize line (FIG. 10).

The fluorescent spikes observed in $_{zm}$PSY1-NP-GFP expression experiments were similar to fibrils seen in carotenoid-rich chromoplasts of *Solanum capsicastrum*. In *Solanum*, such fibrillar plastoglobuli initiate from globular plastoglobuli. This morphogenic change is observed together with an increase in carotenoid concentration, although it is unknown what triggers fibril formation. Capacity to accumulate large quantities of carotenoids is characteristic of non-photosynthetic plastids. For example, constitutive overexpression of $_{at}$PSY in *Arabidopsis* resulted in carotenoid bar-shaped crystals (spikes) formed in non-photosynthetic plastids of roots, while no changes were observed in photosynthetic tissues. Similarly, fibrils in green protoplasts were not observed, which might be explained by alternative mechanisms of carotenoid sequestration in chloroplasts as compared to non-photosynthetic plastids. Thus, the results indicate that $_{zm}$PSY1-NP was located in fibrillar plastoglobuli, which initiate from globular plastoglobuli in the presence of high concentrations of carotenoids. The presence of carotenoids in fibrils was supported by the use of Spectral Dye Separation tool in LAS AF software (Leica), applied to the fluorescence intensity spectra of $_{zm}$PSYs-GFP constructs expressed in protoplasts prepared from etiolated leaves of $_{zm}$PSY1-knockout maize (FIG. 11). The Spectral Dye Separation tool extracted fluorescence of carotenoids from total fluorescence in fibrils (or plastoglobuli, as positive control) of transformed protoplasts, suggesting the presence of carotenoids in those locations.

If fibrils formed as a consequence of high carotenoid production from over-expressed PSY, then inactivation of $_{zm}$PSY1-NP-GFP would be predicted to eliminate fibril formation. To test this, the enzyme was inactivated by mutagenesis of the active site. The choice of the active site was based on structural homology of $_{zm}$PSY1 to squalene synthase (SQS), as predicted online by Structure Prediction Meta Server. SQS has a similar catalytic mechanism to PSY and a known crystal structure. The PSY active site and other regions critical for enzyme activity are highly conserved among PSY/SQS family members. Meta Server gave a significant 3D-Jury score of 211 (>50 is considered significant) regarding structural similarity between PSY and SQS. Predicted structural similarities between PSYs and SQS are presented in FIG. 4. Mutagenesis of either of two highly conserved aspartate residues 219 and 223 to glutamate inactivates SQS. Thus, the corresponding aspartate residue 285 to glutamate was mutagenized and $_{zm}$PSY1 (Table 1) was inactivated, which was confirmed by testing for functional complementation in *E. coli*. When the inactive enzyme $_{zm}$PSY1-NP-E-GFP was inactivated in etiolated protoplasts, the plastid morphology was now normal, fibrils no longer formed, and the inactive enzyme showed a stromal localization as found for the active, progenitor enzyme, $_{zm}$PSY1 (FIG. 6).

The Spectral Dye separation tool showed no carotenoid fluorescence signal when protoplasts expressed the inactive enzyme $_{zm}$PSY-NP-E as compared to the positive signal obtained from protoplasts expressing the active enzyme $_{zm}$PSY-NP (FIG. 11). Thus, it is concluded that increased local carotenoid concentration, causing fibril spikes and plastid morphological change, was due to PSY1 enzyme activity.

Example 4: Computer Modeling of PSY Structures Provided Insight into Localization Phenotypes of Mutant Enzymes It was expected that changes in the localization phenotype of $_{zm}$PSY1-NP (compared to $_{zm}$PSY1 and $_{zm}$PSY1-NP-E) were related to structural changes in the protein. To study the effect of various residues at positions 168 and 257 on structure of $_{zm}$PSY1, we used the computational methods of structural homology modeling and molecular modeling. Homology modeling provided initial structural predictions for $_{zm}$PSY1 ("NT"), $_{zm}$PSY1-NP and $_{zm}$PSY1-SP. Selected structural predictions resulting from our homology modeling calculations were then subjected to minimization and molecular dynamics techniques (see methods) to derive our final predicted structures. We aligned the latter two structural predictions against that of our predicted structure of $_{zm}$PSY1. The aligned structures of the $T_{257}$ and $P_{257}$ variants of $_{zm}$PSY1 (FIG. 7A) clearly showed that the overall structure of the enzyme is preserved, in particular the length and relative positions of alpha helices, with some perturbations in a few of the loop domains. The overall root mean square deviation (RMSD) between the two structures was 3.8 angstroms (FIG. 7B, red line). Most notable was the large variation in the loop region around residue 184. The loop is located in close proximity to the $_{159}$DELVD$_{163}$ (SEQ ID NO: 144) region of the enzyme (FIG. 7A), which together with $_{285}$DVGED$_{289}$ (SEQ ID NO: 145) is a conserved sequence among isoprenoid synthases, and forms an active site to bind phosphate groups of a substrate. The deviation between RMSD values of $_{zm}$PSY1 and $_{zm}$PSY1-NP at this region was noted to be significantly larger than 3.8 angstroms. The difference between $_{zm}$PSY1 and $_{zm}$PSY1-SP (FIG. 7B, green line) in the same region, however, was not significant when taking into account the overall average RMSD values difference across the entire protein. This observation suggested that the structure of $_{zm}$PSY1-SP was similar to $_{zm}$PSY1. The similar structure was consistent with the common stromal localization of these two proteins.

This modeling predicted that a change of threonine to proline at position 257 will cause remote structural alterations in PSY1 in the loop region around residue 184, where several mutations were shown to affect PSY activity. For example, a change of the amino acid corresponding to A174 to D increased PSY activity in cassava, while mutagenesis of the amino acid corresponding to P190 to L decreased the activity of PSY1 in tomato (all residue numbers are relative to $_{zm}$PSY1, and shown in FIG. 4 and FIG. 7B in blue).

Thus, as a result of the present invention, it has been shown that a single specific amino acid alteration could have functional and/or localization consequences. The change in residue at critical locations such as at position 257 could change protein folding at a location remote and thus either affect activity of the enzyme by altering substrate affinity, or affect interaction with an upstream enzyme that provides the PSY substrate. Indeed, the $T_{257}$ to $P_{257}$ mutation in the PSY1-GFP fusion caused formation of spikes and altered plastid morphology. A second amino acid change at $S_{168}$ ($S_{168}P_{257}$), however, was able to counteract the structural perturbations caused by $P_{257}$, restoring the structure and specific features of the progenitor $_{zm}$PSY1. Therefore, PSYs with NT or SP are predicted to be structurally similar whereas NP is predicted to cause a structural perturbation.

TABLE 1

PSY variants used in transient expression experiments. Numbers of amino acids are actual numbers in PSY amino acid sequences. Plastid localization is based on the PSY GFP-fusion experiments. Abbreviations: zm, maize; os, rice; at,*Arabidopsis*.

| | PSY variant name | Amino acid variation | Is this a naturally found variant? | Test of activity in *E. coli* | Plastid localization |
|---|---|---|---|---|---|
| Maize | $_{zm}$PSY1 | $N_{168}$; $T_{257}$ | Yes, yellow endosperm lines including B73, and some white endosperm lines | active | Stroma/spots |

TABLE 1-continued

PSY variants used in transient expression experiments. Numbers of amino acids are actual numbers in PSY amino acid sequences. Plastid localization is based on the PSY GFP-fusion experiments. Abbreviations: zm, maize; os, rice; at, *Arabidopsis*.

|  | PSY variant name | Amino acid variation | Is this a naturally found variant? | Test of activity in *E. coli* | Plastid localization |
|---|---|---|---|---|---|
|  | zmPSY1-NP | $N_{168}$; $P_{257}$ | Yes, white endosperm lines | active | fibrils |
|  | zmPSY1-NS | $N_{168}$; $S_{257}$ | Yes, white endosperm lines | — | stroma |
|  | zmPSY1-NP-E | $N_{168}$; $P_{257}$; $E_{285}$ | no | inactive | stroma |
|  | zmPSY1-SP | $S_{168}$; $P_{257}$ | no | — | stroma |
|  | zmPSY1-ST | $S_{168}$; $T_{257}$ | no | — | stroma |
|  | zmPSY2 | $S_{168}$; $P_{257}$ | yes | active[1] | plastoglobuli |
|  | zmPSY2-ST | $S_{168}$; $T_{257}$ | no | — | plastoglobuli |
|  | zmPSY2-NP | $N_{168}$; $P_{257}$ | no | — | plastoglobuli |
|  | zmPSY2-NT | $N_{168}$; $T_{257}$ | no | — | plastoglobuli |
|  | zmPSY3 | $S_{176}$; $P_{265}$ | yes | active[3] | plastoglobuli |
| Rice | osPSY1 | $S_{179}$; $P_{268}$ | yes | active[1] | plastoglobuli |
|  | osPSY1-ST | $S_{179}$; $T_{268}$ | no | — | plastoglobuli |
|  | osPSY2 | $S_{163}$; $P_{253}$ | yes | active[1] | plastoglobuli |
| *Arabidopsis* | atPSY | $S_{181}$; $P_{270}$ | yes | active[2] | plastoglobuli |

TABLE 2

Plasmids and primers used for cloning

| Plasmid | SEQ ID NO: | Primers used for cloning | Restriction sites used for cloning |
|---|---|---|---|
| pTnT-zmPSY1 | 51 | F 5' TCTCGAGATGGCCATCATACTCGTACGAG | XhoI/XbaI |
|  | 52 | R 5' ATCTAGACTAGGTCTGGCCATTTCTCAATG |  |
| pTnT-zmPSY2 | 53 | F 5' ACTCGAGAATGGCTGCGGGCTCGTCCG | XhoI/NotI |
|  | 54 | R 5' GAT GTG ATC TAC GGA TGG TTC AT |  |
| pTnT-zmPSY3 | 55 | F 5' AAGAATTCGCCACCATGATGTCTACGAGC | EcoRI + Kozak sequence, NotI |
|  | 56 | R 5' AAGCGGCCGCCTATGTTAGGGTGGAATAGC |  |
| pUC35S-zmPSY1-sGFP-Nos | 57 | F 5' TTCTAGAATGGCCATCATACTCGTACGAG | XbaI/BamHI |
|  | 58 | R 5' AGGATCCGGTCTGGCCATTTCTCAATGAA |  |
| pUC35S-zmPSY2-sGFP-Nos | 59 | F 5' ATCTAGAATGGCTGCGGGCTCGTCC | XbaI/BamHI |
|  | 60 | R 5' AGGATCCTGGTGCAACCGCAGCCCTTGCA |  |
| pUC35S-zmPSY3-sGFP-Nos | 61 | F 5' ATCTCTAGAATGATGTCTACGAGCCGCGCGGTGAAGTCG | XbaI/BamHI |
|  | 62 | R 5' ATCGGATCCTGTTAGGGTGGAATAGCGTCTCCGGCTC |  |
| pUC35S-osPSY1-sGFP-Nos | 63 | F 5' ATCTAGAATGGCCCATCACGCTCCTAC | XbaI/BgII |
|  | 64 | R 5' A AGATCT CTT CTG GCT ATT TCT CAG TGA G |  |
| pUC35S-osPSY2-sGFP-Nos | 65 | F 5' AAC TAG TTC CAC ACG AAC ACA CAA CCC CAA | SpeI/BgII |
|  | 66 | R 5' AAGATCTTGATGCAACTGCCGCTCTTGCATA |  |
| pUC35S-LHCP-sGFP-Nos | 67 | F 5' ATCTCTAGAATGGCCGCTTCATCC | XbaI/BamHI |
|  | 68 | R 5' ATCGGATCCCTTTCCGGGAACAAAGTTGGTAGC |  |
| pSAT-atPSY-RFP | 69 | F 5' ATCGAATTCATGTCTTCTTCTGTAGCAGTG | EcoRI/BamHI |
|  | 70 | R 5' ATTGGATCCGTATCGATAGTCTTGAACTTG |  |
| pSAT-zmPG2-RFP | 71 | F 5' ATCGAATTCATGGCMCCTCCGCGTTCCTCAACG | EcoRI/BcII |
|  | 72 | R 5' ATCTGATCAGGTATAGAAGAGTACTTCCC |  |
| pUC35S-zmPSY1-NP-sGFP-Nos | 73 | F 5' CCTGTGATGGGCATCGCACCCGAGTCTAAAG | — |
|  | 74 | R 5' CTTTAGACTCGGGTGCGATGCCCATCACAGG |  |
| pUC35S-zmPSY1-SP-sGFP-Nos | 75 | F 5' CCTGTGATGGGCATCGCACCCGAGTCTAAAG | — |
|  | 76 | R 5' CTTTAGACTCGGGTGCGATGCCCATCACAGG |  |
|  | 77 | F 5' GATGGGCCAAACGCCAGCTACATTACACCAACAG |  |
|  | 78 | R 5' CTGTTGGTGTAATGTAGCTSGCGTTTGGCCCATC |  |
| pUC35S-zmPSY1-NS-sGFP-Nos | 79 | F 5' CCTGTGATGGGCATCGCATCCGAGTCTAAAG | — |
|  | 80 | R 5' CTTTAGACTCGGATGCGATGCCCATCACAGG |  |

TABLE 2-continued

Plasmids and primers used for cloning

| Plasmid | SEQ ID NO: | Primers used for cloning | Restriction sites used for cloning |
|---|---|---|---|
| pUC35S-$_{zm}$PSY1-ST-sGFP-Nos | 81 | F 5' GATGGGCCAAACGCCAGCTACATTACACCAACAG | — |
|  | 82 | R 5' CTGTTGGTGTAATMAGOGGCGTTTGGCCCATC |  |
| pUC35S-$_{zm}$PSY2-ST-sGFP-Nos | 83 | F 5' CCTGTCATGGGCATCGCTACCGACTCCAA | — |
|  | 84 | R 5' TTGGAGTCGGTAGCGATGCCCATGACAGG |  |
| pUC35S-$_{zm}$PSY2-NT-sGFP-Nos | 85 | F 5' CCTGTCATGGGCATCGCTACCGACTCCAA | — |
|  | 86 | R 5' TTGGAGTCGGTAGCGATGCCCATGACAGG |  |
|  | 87 | F 5' GACGGTCCCAACGCGAACTACATCACGCCGAC |  |
|  | 88 | R 5' GTCGGCGTGATGTAGTTCGCGTTGGGACCGTC |  |
| pSAT-$_{zm}$PSY2-NP-RFP | 89 | F 5' GACGGTCCCAACGCGAACTACATCACGCCGAC | — |
|  | 90 | R 5' GTCGGCGTGATGTAGTTCGCGTTGGGACCGTC |  |
| pUC35S-$_{os}$PSY1-NT-sGFP-Nos | 91 | F 5' GTTCCTGTGATGGGTATTGCAACCGAGTCGAAG | — |
|  | 92 | R 5' 5' CTTCGACTCGGTTGCAATACCCATCACAGGAAC |  |
| pBS-$_{zm}$PSY1-NP | 93 | F 5' CCTGTGATGGGCATCGCACCCGAGTCTAAAG | — |
|  | 94 | R 5' CTTTAGACTCGGGTGCGATGCCCATCACAGG |  |
| pBS-$_{zm}$PSY1-D$_{285}$E | 95 | F 5' CGAACATACTCCGGGAGGTTGGAGAGGATGCTA | — |
|  | 96 | R 5' TAGCATCCTCTCCAACCTCCCGGAGTATGTTCG |  |
| pUC35S-$_{zm}$PSY1-NP-E-sGFP-Nos | 97 | F 5' CGAACATACTCCGGGAGGTTGGAGAGGATGCTA | — |
|  | 98 | R 5' TAGCATCCTCTCCAACCTCCCGGAGTATGTTCG |  |
|  | 99 | F 5' CCTGTGATGGGCATCGCACCCGAGTCTAAAG |  |
|  | 100 | R 5' CTTTAGACTCGGGTGCGATGCCCATCACAGG |  |

SEQUENCE LISTING

The instant application contains a Sequence Listing which has been submitted electronically in computer-readable ASCII format and is hereby incorporated by reference in its entirety. Said ASCII copy, created on Jul. 16, 2015, is named 1038-77PCT0US_SL.txt and is 64,198 bytes in size.

The invention claimed is:

1. A method for providing increased carotenoid content to a plant comprising expressing an allelic variant of phytoene synthase 1 (PSY1) in non-photosynthetic plastids of said plant, wherein said non-photosynthetic plastid does not naturally comprise said variant or does not naturally express said variant and the allelic variant has amino acid residues N and P at the respective positions corresponding to amino acid positions 168 and 257 of SEQ ID NO: 1.

2. A method for providing improved stress resistance to climate changes to a plant comprising expressing an allelic variant of phytoene synthase 1 (PSY1) in non-photosynthetic plastids of said plant, wherein said non-photosynthetic plastid does not naturally comprise said variant or does not naturally express said variant and the allelic variant has amino acid residues N and P at the respective positions corresponding to amino acid positions 168 and 257 of SEQ ID NO: 1.

3. A method for selecting plants with increased carotenoid content comprising selecting a plant in which an allelic variant of phytoene synthase 1 (PSY1) is expressed are in non-photosynthetic plastids of said plant, wherein said non-photosynthetic plastid does not naturally comprise said variant or does not naturally express said variant and the allelic variant has amino acid residues N and P at the respective positions corresponding to amino acid positions 168 and 257 of SEQ ID NO: 1.

4. A method for selecting plants having improved stress resistance to climate changes comprising selecting a plant in which an allelic variant of phytoene synthase 1 (PSY1) is expressed are in non-photosynthetic plastids of said plant, wherein said non-photosynthetic plastid does not naturally comprise said variant or does not naturally express said variant and the allelic variant has amino acid residues N and P at the respective positions corresponding to amino acid positions 168 and 257 of SEQ ID NO: 1.

* * * * *